(12) United States Patent
Unger

(10) Patent No.: US 6,632,671 B2
(45) Date of Patent: Oct. 14, 2003

(54) NANOPARTICLE ENCAPSULATION SYSTEM AND METHOD

(75) Inventor: Gretchen M. Unger, Chaska, MN (US)

(73) Assignee: Genesegues, Inc., Chaska, MN (US)

( * ) Notice: Subject to any disclaimer, the term of this patent is extended or adjusted under 35 U.S.C. 154(b) by 0 days.

(21) Appl. No.: 09/796,575

(22) Filed: Feb. 28, 2001

(65) Prior Publication Data

US 2003/0170893 A1 Sep. 11, 2003

Related U.S. Application Data

(60) Provisional application No. 60/185,282, filed on Feb. 28, 2000.

(51) Int. Cl.$^7$ ........................ C12N 15/88; A61K 9/127; A61K 9/51; B01F 3/00; B01J 13/00

(52) U.S. Cl. ........................ 435/455; 435/458; 424/450; 424/451; 424/455; 424/456; 424/489; 514/2; 514/23; 514/42; 514/43; 514/44; 516/9; 264/4.1

(58) Field of Search ........................ 424/450, 451, 424/455, 456, 489; 435/455, 458; 264/4.1; 516/9; 514/2, 23, 42, 43, 44

(56) References Cited

U.S. PATENT DOCUMENTS

| | | | |
|---|---|---|---|
| 4,107,288 A | 8/1978 | Oppenheim et al. ........... 424/22 |
| 4,177,177 A | 12/1979 | Vanderhoff et al. ..... 260/29.2 M |
| 4,913,908 A | 4/1990 | Couvreur et al. ........... 424/501 |
| 4,920,016 A | 4/1990 | Allen et al. |
| 4,937,119 A | 6/1990 | Nikles et al. |
| 4,968,350 A | 11/1990 | Bindschaedler et al. ..... 106/170 |
| 5,133,908 A | 7/1992 | Stainmesse et al. ......... 264/4.1 |
| 5,145,684 A * | 9/1992 | Liversidge et al. ......... 424/489 |
| 5,384,133 A | 1/1995 | Boyes et al. ................ 424/501 |
| 5,439,686 A | 8/1995 | Desai et al. ................ 424/451 |
| 5,498,421 A | 3/1996 | Grinstaff et al. ............ 424/450 |
| 5,503,851 A | 4/1996 | Mank et al. ................ 424/489 |
| 5,516,507 A | 5/1996 | N'Guyen et al. |
| 5,578,709 A | 11/1996 | Woiszwillo ................ 530/410 |
| 5,629,021 A | 5/1997 | Wright ........................ 424/489 |
| 5,639,473 A | 6/1997 | Grinstaff et al. ............ 424/450 |
| 5,639,480 A | 6/1997 | Bodmer et al. ............. 424/501 |
| 5,648,095 A | 7/1997 | Illum et al. ................. 424/489 |
| 5,648,097 A | 7/1997 | Nuwayser ................... 424/489 |
| 5,736,156 A | 4/1998 | Burke |
| 5,759,582 A | 6/1998 | Leong et al. ................ 424/492 |
| 5,858,398 A * | 1/1999 | Cho ............................ 424/450 |
| 5,874,111 A | 2/1999 | Maitra et al. ................ 424/499 |
| 5,916,803 A | 6/1999 | Sedlacek et al. ......... 435/320.1 |
| 5,962,427 A | 10/1999 | Goldstein et al. ............. 514/44 |
| 5,962,566 A | 10/1999 | Grandfils et al. ........... 524/378 |
| 5,985,832 A | 11/1999 | Roodman et al. |
| 5,990,089 A | 11/1999 | Szoka, Jr. et al. ............ 514/44 |
| 6,033,645 A | 3/2000 | Unger et al. |
| 6,051,258 A | 4/2000 | Kantor ....................... 424/491 |
| 6,136,295 A | 10/2000 | Edwards et al. ............... 424/45 |
| 6,139,870 A | 10/2000 | Verrecchia ................... 424/450 |
| 6,143,037 A | 11/2000 | Goldstein et al. ............. 623/66 |
| 6,143,211 A | 11/2000 | Mathiowitz et al. ........... 264/4 |
| 6,146,663 A | 11/2000 | Bissery et al. .............. 424/489 |
| 6,165,440 A | 12/2000 | Esenaliev .................. 424/1.11 |
| 6,165,988 A | 12/2000 | Noe et al. ..................... 514/44 |
| 6,177,103 B1 | 1/2001 | Pace et al. .................. 424/489 |
| 6,197,346 B1 | 3/2001 | Mathiowitz et al. ........ 424/493 |
| 6,322,805 B1 * | 11/2001 | Kim et al. .................. 424/426 |
| 6,372,714 B1 * | 4/2002 | Tanaka et al. ................. 514/2 |

FOREIGN PATENT DOCUMENTS

| | | | |
|---|---|---|---|
| EP | 0 860 167 A1 | 8/1988 | ........... A61K/9/51 |
| WO | WO 88/08011 | 10/1988 | ............... C08J/3/14 |
| WO | WO 97/03702 | 6/1997 | .......... A61K/48/00 |
| WO | WO 98/43664 | 10/1998 | .......... A61K/38/16 |
| WO | WO 99/00113 | 1/1999 | ............ A61K/9/22 |
| WO | WO 99/33558 | 7/1999 | ............ B01J/13/04 |
| WO | WO 00/47130 | 8/2000 | ............ A61F/2/02 |

OTHER PUBLICATIONS

Modlin, Robert L. (2000): A Toll for DNA vaccines. Nature (408): 659–660.

Noonberg, B., et al., (1993): *Characteristics of Oligonucleotide Uptake in Human Keratinocyte Cultures.* The Journal of Investigative Dermatology (101):727–731.

Gerner et al., (1998): *Similarity Between Nuclear Matrix Proteins of Various Cells Revealed by an Improved Isolation Method.* Journal of Cellular Biochemistry (71):363–374.

Quintanar–Guerrero et al., (1998): *Preparation Techniques and Mechanisms of Formation of Biodegradable Nanoparticles from Preformed Polymers.* Drug Development and Industrial Pharmacy, 24(12): 1113–1128.

Golan et al., (1999): *DNA Toroids: Stages in Condensation,* Biochemistry (38): 14069–14076.

Yuan et al., (1994): *Microvascular Permeability and Interstitial Penetration of Sterically Stabilized (Stealth) Liposomes in a Human Tumor Xenograft*[1] Cancer Research (54): 3352–3356.

(List continued on next page.)

*Primary Examiner*—David Guzo
*Assistant Examiner*—David A. Lambertson
(74) *Attorney, Agent, or Firm*—Patterson, Thuente, Skaar & Christensen, P.A.

(57) ABSTRACT

The present invention generally relates to nanocapsules and methods of preparing these nanocapsules. The present invention includes a method of forming a surfactant micelle and dispersing the surfactant micelle into an aqueous composition having a hydrophilic polymer to form a stabilized dispersion of surfactant micelles. The method further includes mechanically forming droplets of the stabilized dispersion of surfactant micelles, precipitating the hydrophilic polymer to form precipitated nanocapsules, incubating the nanocapsules to reduce a diameter of the nanocapsules, and filtering or centrifuging the nanocapsules.

47 Claims, 7 Drawing Sheets

OTHER PUBLICATIONS

Göpferich, Achim, (1995): *Polymer Degradation and Erosion: Mechanisms and Applications.* Eur J. Pharm. Biophar 42(1):1–11.

Brannon–Peppas, (1997): *Polymers in Controlled Drug Delivery.* Medical Plastics and Biomaterials Magazine: 1–17.

Zhang et al., (1997): *Comparison of Integrins in Human Skin, Pig Skin, and Perfused Skin: An In Vitro skin Toxicology Model.* Journal of Applied Toxicology 17(4): 247–253.

Akhtar, et al., (2000): *The delivery of antisense therapeutics.* Advanced Drug Delivery Reviews (44): 3–21.

Dokka et al., (2000): *Novel non–endocyte delivery of antisense oligonucleotides,* Advanced Drug Delivery Reviews (44): 35–49.

Brand et al., (2000): *Transdermal delivery of antisense compounds.* Advanced Drug Delivery Reviews (44): 51–57.

Bally et al., (1999) "Biological barriers to cellular delivery of lipid–based DNA carriers", *Advanced Drug Delivery Reviews (38)*:291–315.

Gaur et al., (2000): *Biodistribution of fluoresceinated dextran using novel nanoparticles evading reticuloendothelial system,* International Journal of Pharmaceutics (202):1–10.

Li et al., (2000): *Nonviral gene therapy: promises and challenges,* Gene Therapy (7): 31–34.

Rolland, A. P. (1998): *From Genes to Gene Medicines: Recent Advances in Nonviral Gene Delivery.* Critical Reviews™ in Therapeutic Drug Carrier Systems 15(2): 143–198.

Kibbe, Arthur, H., Editor, (1986): *Handbook of Pharmaceutical Excipients,* American Pharmaceutical Association, $3^{rd}$ Ed. pp. 94–95, 117–120.

Barry, Brian W. Dermatological Formulations: Percutaneous Absorption, pp. 127–351.

Liberman, H. A., et al. (1996): *Pharmaceutical Dosage Forms: Disperse Systems,* vol. 2, $2^{nd}$ Ed. pp. 1–109.

Dean, J. A., *Lange's Handbook of Chemistry,* $15^{th}$ Ed pp. 1.74 to 1.343, 10.69 to 10.73.

Smith, E. W., et al., *(1995): Percutaneous Penetration Enhancers,* pp. 1–20.

Lide, D. R., Editor in Chief (1922): *CRC Handbook of Chemistry and Physics: A Ready–Reference Book of Chemical and Physical Data,* Chemical Rubber Publishing Co., $81^{st}$ pp. 7–7 to 7–9; 16–10 to 16–11; 16–43 to 16–47; Appendix.

(1934): *Perry's Chemical Engineers' Handbook,* 7th Ed. pp. 2–24 to 2–47.

Gennaro, A. R. *Remington: The Science and Practice of Pharmacy,* $20^{th}$ Ed., Lippincott Williams & Wilkins, pp. 288–334, 721–752, 836–857 and 903–929.

Bronaugh, *R. L., et al.,Editors* (1999): *Percutaneous Absorption Drugs–Cosmetics–Mechanisms–Methodology,* $3^{rd}$ Ed. pp. 177–193, 597–613 and 879–886.

Damgé, C. et al. (1996): *Intestinal absorption of PLAGA microspheres in the rat,* J. Anat (189): 491–501.

Kreuter, J. (1996): *Mini–review: Nanoparticle and microparticles for drug and vaccine delivery,* J. Anat. (189): 503–505.

Calvo, Pilar et al., (1995): *Comparative in vitro Evaluation of Several Colloidal Systems, Nanoparticles, Nanocapsules, and Nanoemulstions, as Ocular Drug Carriers,* Journal of Pharmaceutical Sciences, 85 (5): 530–536.

Schmidt, Christoph et al., (1999): *Incorporation of polymeric nanoparticles into solid dosage forms,* Journal of Controlled Release (57): 115–125.

Vile, RG et al., (2000): *Millenium Review: Cancer gene therapy: hard lessons and new courses,* Gene Therapy (7): 2–8.

Ash, Michael et al., (1993): *Handbook of Industrial Surfactants,* Gower Publishing Co., pp. 885–905.

Sigma Company Catalog, (1999): *Sigma Biochemicals and Reagents FOR Life Science Research,* St Louis, MO, p. 1918.

Calvo, Pilar et al., *Evaluation of cationic polymer–coated nanocapsules as ocular drug carriers,* International Journal of Pharmaceutics (1997), pp. 41–50.

Kreuter, Jörg, *Nanoparticles–based drug delivery systems,* Journal of Controlled Relese (1991), pp. 169–176.

Lamaze, Christophe et al., *The emergence of clathrin–independent pinocytic pathways,* Current Opinion in Cell Biology (1995), pp. 573–580.

Kreuter, Jörg, *Naoparticles—Preparation And Applications,* Microcapsules and Nanoparticles in Medicine and Pharmacy, pp. 125–148.

Pinto, J.F. et al., *Pellets as carriers of solid lipid nanoparticles (SLN) for oral administration of drugs,* Pharmazie (1999), pp. 506–509.

Kawashima, Yoshiaki, *Nanoparticle systems for improved drug delivery,* Advanced Drug Delivery Reviews (2001), pp. 1–2.

Müller, R.H. et al., *Nanosuspensions as particulate drug formulations in therapy Rationale for deveopment and what we can expect for the future,* Advanced Drug Delivery Reviews (2001), pp. 3–19.

Kreuter, Jörg, *Nanoparticulate systems for brain delivery of drugs,* Advanced Drug Delivery Reviews (2001), pp. 65–81.

Janes, K. A. et al., *Polysaccharide colloidal particles as delivery systems for macromolecules,* Advanced Drug Delivery Reviews (2001), pp. 83–97.

Katoaka, Kazunori et al., *Block copolymer micelles for drug delivery: design, characterization and biological significance,* Advanced Drug Delivery Reviews (2001), pp. 113–131.

Sakuma, Shinji et al., *Design of nanoparticles composed of graft copolymers for oral peptide delivery,* Advanced Drug Delivery Reviews (2001), pp. 21–37.

Takeuchi, Hirofumi et al., *Mucoadhesive nanoparticle systems for peptide drug delivery,* Advanced Drug Delivery Reviews (2001), pp. 39–54.

Nishioka, Yukiko et al., *Lymphatic targeting with nanoparticulate system,* Advanced Drug Delivery Reviews (2001), pp. 55–64.

\* cited by examiner

Nanocapsules prepared under different dispersion conditions.

Cumulative release studies for nanocapsule formulations.

Quantitative recovery of DNA from receiver solutions.

Nanocapsule modulation of cellular uptake.

Dose response for a nanocapsule formula.

Nanocapsule-delivered transgene production in porcine dermis.

Macromolecule delivery across keratinized barrier epithelia.

Incorporation of nanocapsules into a suture coating.

PVP nanocapsules are taken up by fibroblasts but not keratinocytes.

Nanocapsule design for tumor-targeting.

Nanocapsule coating design for increased drug safety.

Cellular uptake and lysosomal sequestration of RNA oligomers complexed with polyethyleneimine.

Nanocapsules avoid lysosomal sequestration at 18 hours postaddition.

SEQUENCE LISTING

<160> NUMBER OF SEQ ID NOS: 5

<210> SEQ ID NO 1
<211> LENGTH: 6232
<212> TYPE: DNA
<213> ORGANISM: Artificial Sequence
<220> FEATURE:
<223> OTHER INFORMATION: Supplied by Invitrogen of Carlsbad, California

<400> SEQUENCE: 1

```
gtaccgaatt caagcttcgt gaggctccgg tgcccgtcag tgggcagagc gcacatcgcc      60
cacagtcccc gagaagttgg ggggaggggt cggcaattga accggtgcct agagaaggtg     120
gcgcggggta aactgggaaa gtgatgtcgt gtactggctc cgccttttc ccgagggtgg      180 gggagaaccg tatataagtg cagtagtcgc cgtgaacgtt cttttcgca acgggtttgc      240 cgccagaaca caggtaagtg ccgtgtgtgg ttcccgcggg cctggcctct ttacgggtta     300
tggcccttgc gtgccttgaa ttacttccac ctggctccag tacgtgattc ttgatcccga     360
gctggagcca ggggcgggcc ttgcgcttta ggagcccctt cgcctcgtgc ttgagttgag     420
gcctggcctg ggcgctgggg ccgccgcgtg cgaatctggt ggcaccttcg cgcctgtctc     480
gctgctttcg ataagtctct agccatttaa aatttttgat gacctgctgc gacgcttttt     540
ttctggcaag atagtcttgt aaatgcgggc caggatctgc acactggtat ttcggttttt     600
gggcccgcgg ccggcgacgg ggcccgtgcg tcccagcgca catgttcggc gaggcggggc     660
ctgcgagcgc ggccaccgag aatcggacgg gggtagtctc aagctggccg gcctgctctg     720
gtgcctggcc tcgcgccgcc gtgtatcgcc ccgccctggg cggcaaggct ggcccggtcg     780
gcaccagttg cgtgagcgga aagatggccg cttcccggcc ctgctccagg gggctcaaaa     840
tggaggacgc ggcgctcggg agagcgggcg ggtgagtcac ccacacaaag gaaaagggcc     900
tttccgtcct cagccgtcgc ttcatgtgac tccacggagt accgggcgcc gtccaggcac     960
ctcgattagt tctggagctt ttggagtacg tcgtctttag gttggggga ggggttttat    1020 gcgatggagt ttccccacac tgagtgggtg gagactgaag ttaggccagc ttggcacttg    1080
atgtaattct ccttggaatt tggccttttt gagtttggat cttggttcat tctcaagcct    1140
cagacagtgg ttcaaagttt ttttcttcca tttcaggtgt cgtgaacacg tggccaccat    1200
ggcccaggtg cagctgcaga tggctagcaa aggagaagaa cttttcactg gagttgtccc    1260
aattcttgtt gaattagatg gtgatgttaa tgggcacaaa ttttctgtca gtggagaggg    1320
tgaaggtgat gctacatacg gaaagcttac ccttaaattt atttgcacta ctggaaaact    1380
acctgttcca tggccaacac ttgtcactac tttctcttat ggtgttcaat gcttttcccg    1440
ttatccggat catatgaaac ggcatgactt tttcaagagt gccatgcccg aaggttatgt    1500
```

```
acaggaacgc actatatctt tcaaagatga cgggaactac aagacgcgtg ctgaagtcaa    1560
gtttgaaggt gatacccttg ttaatcgtat cgagttaaaa ggtattgatt ttaaagaaga    1620
tggaaacatt ctcggacaca aactcgagta caactataac tcacacaatg tatacatcac    1680
ggcagacaaa caaaagaatg gaatcaaagc taacttcaaa attcgccaca acattgaaga    1740
tggatccgtt caactagcag accattatca acaaaatact ccaattggcg atggccctgt    1800 cctttttacca gacaaccatt acctgtcgac acaatctgcc ctttcgaaag atcccaacga    1860
aaagcgtgac cacatggtcc ttcttgagtt tgtaactgct gctgggatta cacatggcat    1920
ggatgagctc tacaaagcgg ccgcagatcc aaaaaagaag agaaaggtag atccaaaaaa    1980
gaagagaaag gtagatccaa aaaagaagag aaaggtagat acggccgcag aacaaaaact    2040
catctcagaa gaggatctga atggggccgc atagtctaga agctcgctga tcagcctcga    2100
ctgtgccttc tagttgccag ccatctgttg tttgccccctc ccccgtgcct tccttgaccc    2160
tggaaggtgc cactcccact gtcctttcct aataaaatga ggaaattgca tcgcattgtc    2220
tgagtaggtg tcattctatt ctggggggtg ggtggggca ggacagcaag ggggaggatt    2280
gggaagacaa tagcaggcat gctggggatg gcccgggctc tatggcttct gaggcggaaa    2340
gaaccagctg gggctctagg gggtatcccc acgcgccctg tagcggcgca ttaagcgcgg    2400
cgggtgtggt ggttacgcgc agcgtgaccg ctacacttgc cagcgcccta gcgcccgctc    2460
ctttcgcttt cttcccttcc tttctcgcca cgttcgccgg ctttccccgt caagctctaa    2520
atcggggcat ccctttaggg ttccgattta gtgctttacg gcacctcgac cccaaaaaac    2580
ttgattaggg tgatggttca cgtagtgggc catcgccctg atagacggtt tttcgccctt    2640
tgacgttgga gtccacgttc tttaatagtg gactcttgtt ccaaactgga acaacactca    2700
accctatctc ggtctattct tttgatttat aagggatttt ggggatttcg gcctattggt    2760
taaaaaatga gctgatttaa caaaaattta acgcgaatta attctgtgga atgtgtgtca    2820
gttagggtgt ggaaagtccc caggctcccc aggcaggcag aagtatgcaa agcatgcatc    2880
tcaattagtc agcaaccagg tgtggaaagt ccccaggctc cccagcaggc agaagtatgc    2940
aaagcatgca tctcaattag tcagcaacca tagtcccgcc cctaactccg cccatcccgc    3000
ccctaactcc gcccagttcc gcccattctc cgccccctagg ctgactaatt ttttttatt    3060 atgcagaggc cgaggccgcc tctgcctctg agctattcca gaagtagtga ggaggctttt    3120
ttggaggcct aggcttttgc aaaaagctcc cgggaggtcc acaatgattg aacaagatgg    3180
attgcacgca ggttctccgg ccgcttgggt ggagaggcta ttcggctatg actgggcaca    3240
acagacaatc ggctgctctg atgccgccgt gttccggctg tcagcgcagg gcgcccggt    3300 tcttttttgtc aagaccgacc tgtccggtgc cctgaatgaa ctccaggacg aggcagcgcg    3360
gctatcgtgg ctggccacga cgggcgttcc ttgcgcagct gtgctcgacg ttgtcactga    3420
agcgggaagg gactggctgc tattgggcga agtgccgggg caggatctcc tgtcatctca    3480
ccttgctcct gccgagaaag tatccatcat ggctgatgca atgcggcggc tgcatacgct    3540
tgatccggct acctgcccat tcgaccacca agcgaaacat cgcatcgagc gagcacgtac    3600
tcggatggaa gccggtcttg tcgatcagga tgatctggac gaagagcatc aggggctcgc    3660
gccagccgaa ctgttcgcca ggctcaaggc gcgtatgccc gacggcgagg atctcgtcgt    3720
gactcatggc gatgcctgct tgccgaatat catggtggaa aatggccgct ttctggatt    3780 catcgactgt ggccggctgg gtgtggcgga ccgctatcag gacatagcgt tggctacccg    3840
tgatattgct gaagagcttg gcggcgaatg ggctgaccgc ttcctcgtgc tttacggtat    3900
```

```
cgccgctccc gattcgcagc gcatcgcctt ctatcgcctt cttgacgagt tcttctgagc    3960
gggactctgg ggttcgaaat gaccgaccaa gcgacgccca acctgccatc acgagatttc    4020
gattccaccg ccgccttcta tgaaaggttg ggcttcggaa tcgttttccg ggacgccggc    4080
tggatgatcc tccagcgcgg ggatctcatg ctggagttct tcgcccaccc caacttgttt    4140
attgcagctt ataatggtta caaataaagc aatagcatca caaatttcac aaataaagca    4200 ttttttcac tgcattctag ttgtggtttg tccaaactca tcaatgtatc ttatcatgtc    4260
tgtataccgg atctttccgc ttcctcgctc actgactcgc tgcgctcggt cgttcggctg    4320
cggcgagcgg tatcagctca ctcaaaggcg gtaatacggt tatccacaga atcaggggat    4380
aacgcaggaa agaacatgtg agcaaaaggc cagcaaaagg ccaggaaccg taaaaaggcc    4440
gcgttgctgg cgttttccca taggctccgc cccctgacg agcatcacaa aaatcgacgc    4500
tcaagtcaga ggtggcgaaa cccgacagga ctataaagat accaggcgtt tccccctgga    4560
agctccctcg tgcgctctcc tgttccgacc ctgccgctta ccggatacct gtccgccttt    4620
ctcccttcgg gaagcgtggc gctttctcaa tgctcacgct gtaggtatct cagttcggtg    4680
taggtcgttc gctccaagct gggctgtgtg cacgaacccc ccgttcagcc cgaccgctgc    4740
gccttatccg gtaactatcg tcttgagtcc aacccggtaa gacacgactt atcgccactg    4800
gcagcagcca ctggtaacag gattagcaga gcgaggtatg taggcggtgc tacagagttc    4860
ttgaagtggt ggcctaacta cggctacact agaaggacag tatttggtat ctgcgctctg    4920
ctgaagccag ttaccttcgg aaaaagagtt ggtagctctt gatccggcaa acaaaccacc    4980
gctggtagcg gtggtttttt tgtttgcaag cagcagatta cgcgcagaaa aaaggatct    5040 caagaagatc ctttgatctt ttctacgggg tctgacgctc agtggaacga aaactcacgt    5100
taagggattt tggtcatgag attatcaaaa aggatcttca cctagatcct tttaaattaa    5160
aaatgaagtt ttaaatcaat ctaaagtata tatgagtaaa cttggtctga cagttaccaa    5220
tgcttaatca gtgaggcacc tatctcagcg atctgtctat ttcgttcatc catagttgcc    5280
tgactccccg tcgtgtagat aactacgata cgggagggct taccatctgg ccccagtgct    5340
gcaatgatac cgcgagaccc acgctcaccg gctccagatt tatcagcaat aaaccagcca    5400
gccggaaggg ccgagcgcag aagtggtcct gcaactttat ccgcctccat ccagtctatt    5460
aattgttgcc gggaagctag agtaagtagt tcgccagtta atagtttgcg caacgttgtt    5520
gccattgcta caggcatcgt ggtgtcacgc tcgtcgtttg gtatggcttc attcagctcc    5580
ggttcccaac gatcaaggcg agttacatga tcccccatgt tgtgcaaaaa agcggttagc    5640
tccttcggtc ctccgatcgt tgtcagaagt aagttggccg cagtgttatc actcatggtt    5700
atggcagcac tgcataattc tcttactgtc atgccatccg taagatgctt ttctgtgact    5760
ggtgagtact caaccaagtc attctgagaa tagtgtatgc ggcgaccgag ttgctcttgc    5820
ccggcgtcaa tacgggataa taccgcgcca catagcagaa ctttaaaagt gctcatcatt    5880
ggaaaacgtt cttcggggcg aaaactctca aggatcttac cgctgttgag atccagttcg    5940
atgtaaccca ctcgtgcacc caactgatct tcagcatctt ttactttcac cagcgtttct    6000
gggtgagcaa aaacaggaag gcaaaatgcc gcaaaaaagg gaataagggc gacacggaaa    6060
tgttgaatac tcatactctt cctttttcaa tattattgaa gcatttatca gggttattgt    6120
ctcatgagcg gatacatatt tgaatgtatt tagaaaaata aacaaatagg ggttccgcgc    6180
acatttcccc gaaaagtgcc acctgacgtc agatcgacgg atcgggagat cg             6232
```

-continued

```
<210> SEQ ID NO 2
<211> LENGTH: 2200
<212> TYPE: PRT
<213> ORGANISM: Homo sapiens

<400> SEQUENCE: 2
```

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
                20                  25                  30

Arg Gln Ser Gly Val Asn Ala Thr Leu Pro Glu Glu Asn Gln Pro Val
            35                  40                  45

Val Phe Asn His Val Tyr Asn Ile Lys Leu Pro Val Gly Ser Gln Cys
50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
        210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Glu Cys Val Cys Asp Glu Gly
        290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Leu Asp Cys Ser Glu Lys Arg Cys Pro Ala Asp Cys His Asn Arg
        370                 375                 380

```
Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
            405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
            435                 440                 445

Cys Val Glu Gly Lys Cys Val Cys Glu Gln Gly Phe Lys Gly Tyr Asp
450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
            485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
            515                 520                 525

Glu Leu Ser Cys Pro Asn Asp Cys His Gly Gln Gly Arg Cys Val Asn
530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
            565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
            595                 600                 605

Cys Ile Cys Asn Glu Gly Tyr Ser Gly Glu Asp Cys Ser Glu Val Ser
            610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
            645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
            675                 680                 685

Phe Ile Arg Val Phe Ala Ile Leu Glu Asn Lys Lys Ser Ile Pro Val
690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
            725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
            755                 760                 765

Arg Gln Thr Gly Leu Ala Pro Gly Gln Glu Tyr Glu Ile Ser Leu His
            770                 775                 780

Ile Val Lys Asn Asn Thr Arg Gly Pro Gly Leu Lys Arg Val Thr Thr
785                 790                 795                 800
```

-continued

```
Thr Arg Leu Asp Ala Pro Ser Gln Ile Glu Val Lys Asp Val Thr Asp
            805                 810                 815

Thr Thr Ala Leu Ile Thr Trp Phe Lys Pro Leu Ala Glu Ile Asp Gly
        820                 825                 830

Ile Glu Leu Thr Tyr Gly Ile Lys Asp Val Pro Gly Asp Arg Thr Thr
            835                 840                 845

Ile Asp Leu Thr Glu Asp Glu Asn Gln Tyr Ser Ile Gly Asn Leu Lys
        850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
            885                 890                 895

Arg Asn Leu Arg Arg Val Ser Gln Thr Asp Asn Ser Ile Thr Leu Glu
        900                 905                 910

Trp Arg Asn Gly Lys Ala Ala Ile Asp Ser Tyr Arg Ile Lys Tyr Ala
            915                 920                 925

Pro Ile Ser Gly Gly Asp His Ala Glu Val Asp Val Pro Lys Ser Gln
        930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
            965                 970                 975

Ala Thr Ile Asn Ala Ala Thr Glu Leu Asp Thr Pro Lys Asp Leu Gln
        980                 985                 990

Val Ser Glu Thr Ala Glu Thr Ser Leu Thr Leu Leu Trp Lys Thr Pro
            995                 1000                1005

Leu Ala Lys Phe Asp Arg Tyr Arg Leu Asn Tyr Ser Leu Pro Thr
        1010                1015                1020

Gly Gln Trp Val Gly Val Gln Leu Pro Arg Asn Thr Thr Ser Tyr
        1025                1030                1035

Val Leu Arg Gly Leu Glu Pro Gly Gln Glu Tyr Asn Val Leu Leu
        1040                1045                1050

Thr Ala Glu Lys Gly Arg His Lys Ser Lys Pro Ala Arg Val Lys
        1055                1060                1065

Ala Ser Thr Glu Gln Ala Pro Glu Leu Glu Asn Leu Thr Val Thr
        1070                1075                1080

Glu Val Gly Trp Asp Gly Leu Arg Leu Asn Trp Thr Ala Ala Asp
        1085                1090                1095

Gln Ala Tyr Glu His Phe Ile Ile Gln Val Gln Glu Ala Asn Lys
        1100                1105                1110

Val Glu Ala Ala Arg Asn Leu Thr Val Pro Gly Ser Leu Arg Ala
        1115                1120                1125

Val Asp Ile Pro Gly Leu Lys Ala Ala Thr Pro Tyr Thr Val Ser
        1130                1135                1140

Ile Tyr Gly Val Ile Gln Gly Tyr Arg Thr Pro Val Leu Ser Ala
        1145                1150                1155

Glu Ala Ser Thr Gly Glu Thr Pro Asn Leu Gly Glu Val Val Val
        1160                1165                1170

Ala Glu Val Gly Trp Asp Ala Leu Lys Leu Asn Trp Thr Ala Pro
        1175                1180                1185

Glu Gly Ala Tyr Glu Tyr Phe Phe Ile Gln Val Gln Glu Ala Asp
        1190                1195                1200

Thr Val Glu Ala Ala Gln Asn Leu Thr Val Pro Gly Gly Leu Arg
```

-continued

```
              1205                1210                    1215

Ser  Thr  Asp  Leu  Pro  Gly  Leu  Lys  Ala  Ala  Thr  His  Tyr  Thr  Ile
    1220                1225                    1230

Thr  Ile  Arg  Gly  Val  Thr  Gln  Asp  Phe  Ser  Thr  Thr  Pro  Leu  Ser
    1235                1240                    1245

Val  Glu  Val  Leu  Thr  Glu  Glu  Val  Pro  Asp  Met  Gly  Asn  Leu  Thr
    1250                1255                    1260

Val  Thr  Glu  Val  Ser  Trp  Asp  Ala  Leu  Arg  Leu  Asn  Trp  Thr  Thr
    1265                1270                    1275

Pro  Asp  Gly  Thr  Tyr  Asp  Gln  Phe  Thr  Ile  Gln  Val  Gln  Glu  Ala
    1280                1285                    1290

Asp  Gln  Val  Glu  Glu  Ala  His  Asn  Leu  Thr  Val  Pro  Gly  Ser  Leu
    1295                1300                    1305

Arg  Ser  Met  Glu  Ile  Pro  Gly  Leu  Arg  Ala  Gly  Thr  Pro  Tyr  Thr
    1310                1315                    1320

Val  Thr  Leu  His  Gly  Glu  Val  Arg  Gly  His  Ser  Thr  Arg  Pro  Leu
    1325                1330                    1335

Ala  Val  Glu  Val  Val  Thr  Glu  Asp  Leu  Pro  Gln  Leu  Gly  Asp  Leu
    1340                1345                    1350

Ala  Val  Ser  Glu  Val  Gly  Trp  Asp  Gly  Leu  Arg  Leu  Asn  Trp  Thr
    1355                1360                    1365

Ala  Ala  Asp  Asn  Ala  Tyr  Glu  His  Phe  Val  Gln  Val  Gln  Glu  Val
    1370                1375                    1380

Asn  Lys  Val  Glu  Ala  Ala  Gln  Asn  Leu  Thr  Leu  Pro  Gly  Ser  Leu
    1385                1390                    1395

Arg  Ala  Val  Asp  Ile  Pro  Gly  Leu  Glu  Ala  Ala  Thr  Pro  Tyr  Arg
    1400                1405                    1410

Val  Ser  Ile  Tyr  Gly  Val  Ile  Arg  Gly  Tyr  Arg  Thr  Pro  Val  Leu
    1415                1420                    1425

Ser  Ala  Glu  Ala  Ser  Thr  Ala  Lys  Glu  Pro  Glu  Ile  Gly  Asn  Leu
    1430                1435                    1440

Asn  Val  Ser  Asp  Ile  Thr  Pro  Glu  Ser  Phe  Asn  Leu  Ser  Trp  Met
    1445                1450                    1455

Ala  Thr  Asp  Gly  Ile  Phe  Glu  Thr  Phe  Thr  Ile  Glu  Ile  Ile  Asp
    1460                1465                    1470

Ser  Asn  Arg  Leu  Leu  Glu  Thr  Val  Glu  Tyr  Asn  Ile  Ser  Gly  Ala
    1475                1480                    1485

Glu  Arg  Thr  Ala  His  Ile  Ser  Gly  Leu  Pro  Pro  Ser  Thr  Asp  Phe
    1490                1495                    1500

Ile  Val  Tyr  Leu  Ser  Gly  Leu  Ala  Pro  Ser  Ile  Arg  Thr  Lys  Thr
    1505                1510                    1515

Ile  Ser  Ala  Thr  Ala  Thr  Thr  Glu  Ala  Leu  Pro  Leu  Leu  Glu  Asn
    1520                1525                    1530

Leu  Thr  Ile  Ser  Asp  Ile  Asn  Pro  Tyr  Gly  Phe  Thr  Val  Ser  Trp
    1535                1540                    1545

Met  Ala  Ser  Glu  Asn  Ala  Phe  Asp  Ser  Phe  Leu  Val  Thr  Val  Val
    1550                1555                    1560

Asp  Ser  Gly  Lys  Leu  Leu  Asp  Pro  Gln  Glu  Phe  Thr  Leu  Ser  Gly
    1565                1570                    1575

Thr  Gln  Arg  Lys  Leu  Glu  Leu  Arg  Gly  Leu  Ile  Thr  Gly  Ile  Gly
    1580                1585                    1590

Tyr  Glu  Val  Met  Val  Ser  Gly  Phe  Thr  Gln  Gly  His  Gln  Thr  Lys
    1595                1600                    1605
```

```
Pro Leu Arg Ala Glu Ile Val Thr Glu Ala Glu Pro Glu Val Asp
1610                1615                1620

Asn Leu Leu Val Ser Asp Ala Thr Pro Asp Gly Phe Arg Leu Ser
1625                1630                1635

Trp Thr Ala Asp Glu Gly Val Phe Asp Asn Phe Val Leu Lys Ile
1640                1645                1650

Arg Asp Thr Lys Lys Gln Ser Glu Pro Leu Glu Ile Thr Leu Leu
1655                1660                1665

Ala Pro Glu Arg Thr Arg Asp Leu Thr Gly Leu Arg Glu Ala Thr
1670                1675                1680

Glu Tyr Glu Ile Glu Leu Tyr Gly Ile Ser Lys Gly Arg Arg Ser
1685                1690                1695

Gln Thr Val Ser Ala Ile Ala Thr Thr Ala Met Gly Ser Pro Lys
1700                1705                1710

Glu Val Ile Phe Ser Asp Ile Thr Glu Asn Ser Ala Thr Val Ser
1715                1720                1725

Trp Arg Ala Pro Thr Ala Gln Val Glu Ser Phe Arg Ile Thr Tyr
1730                1735                1740

Val Pro Ile Thr Gly Gly Thr Pro Ser Met Val Thr Val Asp Gly
1745                1750                1755

Thr Lys Thr Gln Thr Arg Leu Val Lys Leu Ile Pro Gly Val Glu
1760                1765                1770

Tyr Leu Val Ser Ile Ile Ala Met Lys Gly Phe Glu Glu Ser Glu
1775                1780                1785

Pro Val Ser Gly Ser Phe Thr Thr Ala Leu Asp Gly Pro Ser Gly
1790                1795                1800

Leu Val Thr Ala Asn Ile Thr Asp Ser Glu Ala Leu Ala Arg Trp
1805                1810                1815

Gln Pro Ala Ile Ala Thr Val Asp Ser Tyr Val Ile Ser Tyr Thr
1820                1825                1830

Gly Glu Lys Val Pro Glu Ile Thr Arg Thr Val Ser Gly Asn Thr
1835                1840                1845

Val Glu Tyr Ala Leu Thr Asp Leu Glu Pro Ala Thr Glu Tyr Thr
1850                1855                1860

Leu Arg Ile Phe Ala Glu Lys Gly Pro Gln Lys Ser Ser Thr Ile
1865                1870                1875

Thr Ala Lys Phe Thr Thr Asp Leu Asp Ser Pro Arg Asp Leu Thr
1880                1885                1890

Ala Thr Glu Val Gln Ser Glu Thr Ala Leu Leu Thr Trp Arg Pro
1895                1900                1905

Pro Arg Ala Ser Val Thr Gly Tyr Leu Leu Val Tyr Glu Ser Val
1910                1915                1920

Asp Gly Thr Val Lys Glu Val Ile Val Gly Pro Asp Thr Thr Ser
1925                1930                1935

Tyr Ser Leu Ala Asp Leu Ser Pro Ser Thr His Tyr Thr Ala Lys
1940                1945                1950

Ile Gln Ala Leu Asn Gly Pro Leu Arg Ser Asn Met Ile Gln Thr
1955                1960                1965

Ile Phe Thr Thr Ile Gly Leu Leu Tyr Pro Phe Pro Lys Asp Cys
1970                1975                1980

Ser Gln Ala Met Leu Asn Gly Asp Thr Thr Ser Gly Leu Tyr Thr
1985                1990                1995
```

| | | | | | | | | | | |
|---|---|---|---|---|---|---|---|---|---|---|
| Ile | Tyr | Leu | Asn | Gly | Asp | Lys | Ala | Gln | Ala | Leu | Glu | Val | Phe | Cys |
| | 2000 | | | | 2005 | | | | 2010 | |

Asp Met Thr Ser Asp Gly Gly Gly Trp Ile Val Phe Leu Arg Arg
    2015            2020                 2025

Lys Asn Gly Arg Glu Asn Phe Tyr Gln Asn Trp Lys Ala Tyr Ala
    2030            2035                 2040

Ala Gly Phe Gly Asp Arg Arg Glu Glu Phe Trp Leu Gly Leu Asp
    2045            2050                 2055

Asn Leu Asn Lys Ile Thr Ala Gln Gly Gln Tyr Glu Leu Arg Val
    2060            2065                 2070

Asp Leu Arg Asp His Gly Glu Thr Ala Phe Ala Val Tyr Asp Lys
    2075            2080                 2085

Phe Ser Val Gly Asp Ala Lys Thr Arg Tyr Lys Leu Lys Val Glu
    2090            2095                 2100

Gly Tyr Ser Gly Thr Ala Gly Asp Ser Met Ala Tyr His Asn Gly
    2105            2110                 2115

Arg Ser Phe Ser Thr Phe Asp Lys Asp Thr Asp Ser Ala Ile Thr
    2120            2125                 2130

Asn Cys Ala Leu Ser Tyr Lys Gly Ala Phe Trp Tyr Arg Asn Cys
    2135            2140                 2145

His Arg Val Asn Leu Met Gly Arg Tyr Gly Asp Asn Asn His Ser
    2150            2155                 2160

Gln Gly Val Asn Trp Phe His Trp Lys Gly His Glu His Ser Ile
    2165            2170                 2175

Gln Phe Ala Glu Met Lys Leu Arg Pro Ser Asn Phe Arg Asn Leu
    2180            2185                 2190

Glu Gly Arg Arg Lys Arg Ala
    2195            2200

```
<210> SEQ ID NO 3
<211> LENGTH: 8578
<212> TYPE: DNA
<213> ORGANISM: Artificial Sequence
<220> FEATURE:
<223> OTHER INFORMATION: Supplied by Invitrogen of Carlsbad, California

<400> SEQUENCE: 3
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca caaggcaag gcttgaccga caattgcatg aagaatctgc      180
ttagggttag gcgttttgcg ctgcttcgcg atgtacgggc cagatatacg cgttgacatt     240
gattattgac tagttattaa tagtaatcaa ttacgggtc attagttcat agcccatata      300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
```

-continued

```
ctgcttactg gcttatcgaa attaatacga ctcactatag ggagacccaa gctggctagc      900
gtttaaactt aagcttacca tgggggggttc tcatcatcat catcatcatg gtatggctag      960
catgactggt ggacagcaaa tgggtcggga tctgtacgac gatgacgata aggtacctaa     1020
ggatcagctt ggagttgatc ccgtcgtttt acaacgtcgt gactgggaaa accctggcgt     1080
tacccaactt aatcgccttg cagcacatcc cccttcgcc agctggcgta atagcgaaga     1140
ggcccgcacc gatcgccctt cccaacagtt gcgcagcctg aatggcgaat ggcgctttgc     1200
ctggtttccg gcaccagaag cggtgccgga agctggctg gagtgcgatc ttcctgaggc     1260
cgatactgtc gtcgtcccct caaactggca gatgcacggt tacgatgcgc ccatctacac     1320
caacgtaacc tatcccatta cggtcaatcc gccgtttgtt cccacggaga atccgacggg     1380
ttgttactcg ctcacattta atgttgatga agctggcta caggaaggcc agacgcgaat     1440
tatttttgat ggcgttaact cggcgtttca tctgtggtgc aacgggcgct gggtcggtta     1500
cggccaggac agtcgtttgc cgtctgaatt tgacctgagc gcattttttac gcgccggaga     1560
aaaccgcctc gcggtgatgg tgctgcgttg gagtgacggc agttatctgg aagatcagga     1620
tatgtggcgg atgagcggca ttttccgtga cgtctcgttg ctgcataaac cgactacaca     1680
aatcagcgat ttccatgttg ccactcgctt taatgatgat ttcagccgcg ctgtactgga     1740
ggctgaagtt cagatgtgcg gcgagttgcg tgactaccta cgggtaacag ttttctttatg     1800
gcagggtgaa acgcaggtcg ccagcggcac cgcgcctttc ggcggtgaaa ttatcgatga     1860
gcgtggtggt tatgccgatc gcgtcacact acgtctgaac gtcgaaaacc cgaaactgtg     1920
gagcgccgaa atcccgaatc tctatcgtgc ggtggttgaa ctgcacaccg ccgacggcac     1980
gctgattgaa gcagaagcct gcgatgtcgg tttccgcgag gtgcggattg aaaatggtct     2040
gctgctgctg aacggcaagc cgttgctgat tcgaggcgtt aaccgtcacg agcatcatcc     2100
tctgcatggt caggtcatgg atgagcagac gatggtgcag gatatcctgc tgatgaagca     2160
gaacaacttt aacgccgtgc gctgttcgca ttatccgaac catccgctgt ggtacacgct     2220
gtgcgaccgc tacggcctgt atgtggtgga tgaagccaat attgaaaccc acggcatggt     2280
gccaatgaat cgtctgaccg atgatccgcg ctggctaccg gcgatgagcg aacgcgtaac     2340
gcgaatggtg cagcgcgatc gtaatcaccc gagtgtgatc atctggtcgc tggggaatga     2400
atcaggccac ggcgctaatc acgacgcgct gtatcgctgg atcaaatctg tcgatccttc     2460
ccgcccggtg cagtatgaag gcggcggagc cgacaccacg gccaccgata ttatttgccc     2520
gatgtacgcg cgcgtggatg aagaccagcc cttcccggct gtgccgaaat ggtccatcaa     2580
aaaatggctt tcgctacctg gagagacgcg cccgctgatc ctttgcgaat acgcccacgc     2640
gatgggtaac agtcttggcg gtttcgctaa atactggcag gcgtttcgtc agtatccccg     2700
tttacagggc ggcttcgtct gggactgggt ggatcagtcg ctgattaaat atgatgaaaa     2760
cggcaacccg tggtcggctt acggcggtga ttttggcgat acgccgaacg atcgccagtt     2820
ctgtatgaac ggtctggtct tgccgaccg cacgccgcat ccagcgctga cggaagcaaa     2880
acaccagcag cagttttttcc agttccgttt atccgggcaa accatcgaag tgaccagcga     2940
atacctgttc cgtcatagcg ataacgagct cctgcactgg atggtggcgc tggatggtaa     3000
gccgctggca agcggtgaag tgcctctgga tgtcgctcca caaggtaaac agttgattga     3060
actgcctgaa ctaccgcagc cggagagcgc cgggcaactc tggctcacag tacgcgtagt     3120
gcaaccgaac gcgaccgcat ggtcagaagc cgggcacatc agcgcctggc agcagtggcg     3180
```

```
tctggcggaa aacctcagtg tgacgctccc cgccgcgtcc cacgccatcc cgcatctgac    3240
caccagcgaa atggattttt gcatcgagct gggtaataag cgttggcaat ttaaccgcca    3300
gtcaggcttt ctttcacaga tgtggattgg cgataaaaaa caactgctga cgccgctgcg    3360
cgatcagttc acccgtgcac cgctggataa cgacattggc gtaagtgaag cgacccgcat    3420
tgaccctaac gcctgggtcg aacgctggaa ggcggcgggc cattaccagg ccgaagcagc    3480
gttgttgcag tgcacggcag atacacttgc tgatgcggtg ctgattacga ccgctcacgc    3540
gtggcagcat caggggaaaa ccttatttat cagccgaaaa acctaccgga ttgatggtag    3600
tggtcaaatg gcgattaccg ttgatgttga agtggcgagc gatacaccgc atccggcgcg    3660
gattggcctg aactgccagc tggcgcaggt agcagagcgg gtaaactggc tcggattagg    3720
gccgcaagaa aactatcccg accgccttac tgccgcctgt tttgaccgct gggatctgcc    3780
attgtcagac atgtataccc cgtacgtctt cccgagcgaa aacggtctgc gctgcgggac    3840
gcgcgaattg aattatggcc cacaccagtg gcgcggcgac ttccagttca acatcagccg    3900
ctacagtcaa cagcaactga tggaaaccag ccatcgccat ctgctgcacg cggaagaagg    3960
cacatggctg aatatcgacg gtttccatat ggggattggt ggcgacgact cctggagccc    4020
gtcagtatcg gcggagttcc agctgagcgc cggtcgctac cattaccagt tggtctggtg    4080
tcaaaaataa taaagccgaa ttctgcagat atccagcaca gtggcggccg ctcgagtcta    4140
gagggcccgt ttaaacccgc tgatcagcct cgactgtgcc ttctagttgc cagccatctg    4200
ttgtttgccc ctcccccgtg ccttccttga ccctggaagg tgccactccc actgtccttt    4260
cctaataaaa tgaggaaatt gcatcgcatt gtctgagtag gtgtcattct attctggggg    4320
gtggggtggg gcaggacagc aaggggggagg attgggaaga caatagcagg catgctgggg    4380
atgcggtggg ctctatggct tctgaggcgg aaagaaccag ctggggctct agggggtatc    4440
cccacgcgcc ctgtagcggc gcattaagcg cggcgggtgt ggtggttacg cgcagcgtga    4500
ccgctacact tgccagcgcc ctagcgcccg ctcctttcgc tttcttccct cctttctcg    4560 ccacgttcgc cggctttccc cgtcaagctc taaatcgggg catccctta gggttccgat    4620 ttagtgcttt acggcacctc gaccccaaaa aacttgatta gggtgatggt tcacgtagtg    4680
ggccatcgcc ctgatagacg ttttttcgcc ctttgacgtt ggagtccacg ttctttaata    4740
gtggactctt gttccaaact ggaacaacac tcaaccctat ctcggtctat cttttgatt    4800 tataagggat tttgggatt tcggcctatt ggttaaaaaa tgagctgatt taacaaaaat    4860
ttaacgcgaa ttaattctgt ggaatgtgtg tcagttaggg tgtggaaagt ccccaggctc    4920
cccaggcagg cagaagtatg caaagcatgc atctcaatta gtcagcaacc aggtgtggaa    4980
agtccccagg ctccccagca ggcagaagta tgcaaagcat gcatctcaat tagtcagcaa    5040
ccatagtccc gcccctaact ccgcccatcc cgcccctaac tccgcccagt ccgcccatt    5100 ctccgcccca tggctgacta attttttta tttatgcaga ggccgaggcc gcctctgcct    5160
ctgagctatt ccagaagtag tgaggaggct tttttggagg cctaggcttt tgcaaaaagc    5220
tcccgggagc ttgtatatcc attttcggat ctgatcaaga acaggatga ggatcgtttc    5280 gcatgattga acaagatgga ttgcacgcag gttctccggc cgcttgggtg gagaggctat    5340
tcggctatga ctgggcacaa cagacaatcg gctgctctga tgccgccgtg ttccggctgt    5400
cagcgcaggg gcgcccggtt ctttttgtca gaccgacct gtccggtgcc ctgaatgaac    5460
tgcaggacga ggcagcgcgg ctatcgtggc tggcacgac gggcgttcct tgcgcagctg    5520
tgctcgacgt tgtcactgaa gcgggaaggg actggctgct attgggcgaa gtgccggggc    5580
```

-continued

```
aggatctcct gtcatctcac cttgctcctg ccgagaaagt atccatcatg gctgatgcaa    5640
tgcggcggct gcatacgctt gatccggcta cctgcccatt cgaccaccaa gcgaaacatc    5700
gcatcgagcg agcacgtact cggatggaag ccggtcttgt cgatcaggat gatctggacg    5760
aagagcatca ggggctcgcg ccagccgaac tgttcgccag gctcaaggcg cgcatgcccg    5820
acggcgagga tctcgtcgtg acccatggcg atgcctgctt gccgaatatc atggtggaaa    5880
atggccgctt ttctggattc atcgactgtg gccggctggg tgtggcggac cgctatcagg    5940
acatagcgtt ggctacccgt gatattgctg aagagcttgg cggcgaatgg gctgaccgct    6000
tcctcgtgct ttacggtatc gccgctcccg attcgcagcg catcgccttc tatcgccttc    6060
ttgacgagtt cttctgagcg ggactctggg gttcgaaatg accgaccaag cgacgcccaa    6120
cctgccatca cgagatttcg attccaccgc cgccttctat gaaaggttgg gcttcggaat    6180
cgttttccgg gacgccggct ggatgatcct ccagcgcggg gatctcatgc tggagttctt    6240
cgcccacccc aacttgttta ttgcagctta taatggttac aaataaagca atagcatcac    6300
aaatttcaca aataaagcat ttttttcact gcattctagt tgtggtttgt ccaaactcat    6360
caatgtatct tatcatgtct gtataccgtc gacctctagc tagagcttgg cgtaatcatg    6420
gtcatagctg tttcctgtgt gaaattgtta tccgctcaca attccacaca atacgagc     6480 cggaagcata agtgtaaagc ctggggtgc ctaatgagtg agctaactca cattaattgc    6540
gttgcgctca ctgcccgctt tccagtcggg aaacctgtcg tgccagctgc attaatgaat    6600
cggccaacgc gcggggagag gcggtttgcg tattgggcgc tcttccgctt cctcgctcac    6660
tgactcgctg cgctcggtcg ttcggctgcg gcgagcggta tcagctcact caaaggcggt    6720
aatacggtta tccacagaat cagggataac gcaggaaag aacatgtgag caaaaggcca    6780
gcaaaaggcc aggaaccgta aaaaggccgc gttgctggcg ttttccata ggctccgccc    6840 ccctgacgag catcacaaaa atcgacgctc aagtcagagg tggcgaaacc cgacaggact    6900
ataaagatac caggcgtttc cccctggaag ctccctcgtg cgctctcctg ttccgaccct    6960
gccgcttacc ggatacctgt ccgcctttct cccttcggga agcgtggcgc tttctcaatg    7020
ctcacgctgt aggtatctca gttcggtgta ggtcgttcgc tccaagctgg gctgtgtgca    7080 cgaaccccc gttcagcccg accgctgcgc cttatccggt aactatcgtc ttgagtccaa    7140
cccggtaaga cacgacttat cgccactggc agcagccact ggtaacagga ttagcagagc    7200
gaggtatgta ggcggtgcta cagagttctt gaagtggtgg cctaactacg gctacactag    7260
aaggacagta tttggtatct gcgctctgct gaagccagtt accttcggaa aaagagttgg    7320
tagctcttga tccggcaaac aaaccaccgc tggtagcggt ggttttttg tttgcaagca    7380 gcagattacg cgcagaaaaa aaggatctca agaagatcct ttgatctttt ctacggggtc    7440
tgacgctcag tggaacgaaa actcacgtta agggattttg gtcatgagat tatcaaaaag    7500
gatcttcacc tagatccttt taaattaaaa atgaagtttt aaatcaatct aaagtatata    7560
tgagtaaact tggtctgaca gttaccaatg cttaatcagt gaggcaccta tctcagcgat    7620
ctgtctattt cgttcatcca tagttgcctg actccccgtc gtgtagataa ctacgatacg    7680
ggagggctta ccatctggcc ccagtgctgc aatgataccg cgagacccac gctcaccggc    7740
tccagattta tcagcaataa accagccagc cggaagggcc gagcgcagaa gtggtcctgc    7800
aactttatcc gcctccatcc agtctattaa ttgttgccgg gaagctagag taagtagttc    7860
gccagttaat agtttgcgca acgttgttgc cattgctaca ggcatcgtgg tgtcacgctc    7920
```

-continued

| | |
|---|---|
| gtcgtttggt atggcttcat tcagctccgg ttcccaacga tcaaggcgag ttacatgatc | 7980 |
| ccccatgttg tgcaaaaaag cggttagctc cttcggtcct ccgatcgttg tcagaagtaa | 8040 |
| gttggccgca gtgttatcac tcatggttat ggcagcactg cataattctc ttactgtcat | 8100 |
| gccatccgta agatgctttt ctgtgactgg tgagtactca accaagtcat tctgagaata | 8160 |
| gtgtatgcgg cgaccgagtt gctcttgccc ggcgtcaata cgggataata ccgcgccaca | 8220 |
| tagcagaact ttaaaagtgc tcatcattgg aaaacgttct tcgggcgaaa actctcaag | 8280 |
| gatcttaccg ctgttgagat ccagttcgat gtaacccact cgtgcaccca actgatcttc | 8340 |
| agcatctttt actttcacca gcgtttctgg gtgagcaaaa acaggaaggc aaaatgccgc | 8400 |
| aaaaaaggga ataagggcga cacggaaatg ttgaatactc atactcttcc tttttcaata | 8460 |
| ttattgaagc atttatcagg gttattgtct catgagcgga tacatatttg aatgtattta | 8520 |
| gaaaaataaa caaatagggg ttccgcgcac atttccccga aaagtgccac ctgacgtc | 8578 |

<210> SEQ ID NO 4
<211> LENGTH: 4748
<212> TYPE: DNA
<213> ORGANISM: Artificial Sequence
<220> FEATURE:
<223> OTHER INFORMATION: Provided by Dr. Brett Levay-Young of the
      University of Minnesota

<400> SEQUENCE: 4

| | |
|---|---|
| tagttattaa tagtaatcaa ttacggggtc attagttcat agcccatata tggagttccg | 60 |
| cgttacataa cttacggtaa atggcccgcc tggctgaccg cccaacgacc cccgcccatt | 120 |
| gacgtcaata atgacgtatg ttcccatagt aacgccaata gggactttcc attgacgtca | 180 |
| atgggtggag tatttacggt aaactgccca cttggcagta catcaagtgt atcatatgcc | 240 |
| aagtacgccc cctattgacg tcaatgacgg taaatggccc gcctggcatt atgcccagta | 300 |
| catgacctta tgggactttc ctacttggca gtacatctac gtattagtca tcgctattac | 360 |
| catggtgatg cggttttggc agtacatcaa tgggcgtgga tagcggtttg actcacgggg | 420 |
| atttccaagt ctccacccca ttgacgtcaa tgggagtttg ttttggcacc aaaatcaacg | 480 |
| ggactttcca aaatgtcgta caactccgcc ccattgacg caaatgggcg gtaggcgtgt | 540 |
| acggtgggag gtctatataa gcagagctgg tttagtgaac cgtcagatcc gctagcgcta | 600 |
| ccggtcgcca ccatggtgag caagggcgag gagctgttca ccggggtggt gcccatcctg | 660 |
| gtcgagctgg acggcgacgt aaacggccac aagttcagcg tgtccggcga gggcgagggc | 720 |
| gatgccacct acggcaagct gaccctgaag ttcatctgca ccaccggcaa gctgcccgtg | 780 |
| ccctggccca cccctcgtgac cacctgacc tacggcgtgc agtgcttcag ccgctacccc | 840 |
| gaccacatga agcagcacga cttcttcaag tccgccatgc ccgaaggcta cgtccaggag | 900 |
| cgcaccatct tcttcaagga cgacggcaac tacaagaccc gcgccgaggt gaagttcgag | 960 |
| ggcgacaccc tggtgaaccg catcgagctg aagggcatcg acttcaagga ggacggcaac | 1020 |
| atcctggggc acaagctgga gtacaactac aacagccaca cgtctatat catggccgac | 1080 |
| aagcagaaga acggcatcaa ggtgaacttc aagatccgcc acaacatcga ggacggcagc | 1140 |
| gtgcagctcg ccgaccacta ccagcagaac ccccatcg cgacggcccc cgtgctgctg | 1200 |
| cccgacaacc actacctgag cacccagtcc gccctgagca agacccccaa cgagaagcgc | 1260 |
| gatcacatgg tcctgctgga gttcgtgacc gccgccggga tcactctcgg catggacgag | 1320 |
| ctgtacaagt actcagatct cgagctcaag cttaaccctc cggacgagag cggccctggc | 1380 |

-continued

```
tgtatgtcct gcaagtgcgt gctgtcctga tcaccggatc tagataactg atcataatca    1440
gccataccac atttgtagag gttttacttg cttttaaaaaa cctcccacac ctcccctga    1500 acctgaaaca taaaatgaat gcaattgttg ttgttaactt gtttattgca gcttataatg    1560
gttacaaata aagcaatagc atcacaaatt tcacaaataa agcatttttt tcactgcatt    1620
ctagttgtgg tttgtccaaa ctcatcaatg tatcttaacg cgtaaattgt aagcgttaat    1680
attttgttaa aattcgcgtt aaattttgt taaatcagct cattttttaa ccaataggcc     1740
gaaatcggca aaatccctta taaatcaaaa gaatagaccg atagggtt gagtgttgtt      1800 ccagtttgga acaagagtcc actattaaag aacgtggact ccaacgtcaa agggcgaaaa    1860
accgtctatc agggcgatgg cccactacgt gaaccatcac cctaatcaag ttttttgggg    1920
tcgaggtgcc gtaaagcact aaatcggaac cctaaaggga gccccccgatt tagagcttga   1980 cggggaaagc cggcgaacgt ggcgagaaag gaagggaaga aagcgaaagg agcgggcgct    2040
agggcgctgg caagtgtagc ggtcacgctg cgcgtaacca ccacacccgc cgcgcttaat    2100
gcgccgctac agggcgcgtc aggtggcact tttcggggaa atgtgcgcgg aacccctatt    2160
tgtttatttt tctaaataca ttcaaatatg tatccgctca tgagacaata accctgataa    2220
atgcttcaat aatattgaaa aaggaagagt cctgaggcgg aaagaaccag ctgtggaatg    2280
tgtgtcagtt agggtgtgga agtccccag gctccccagc aggcagaagt atgcaaagca     2340
tgcatctcaa ttagtcagca accaggtgtg gaaagtcccc aggctcccca gcaggcagaa    2400
gtatgcaaag catgcatctc aattagtcag caaccatagt cccgcccta actccgccca    2460 tcccgcccct aactccgccc agttccgccc attctccgcc ccatggctga ctaatttttt    2520
ttatttatgc agaggccgag gccgcctcgg cctctgagct attccagaag tagtgaggag    2580
gcttttttgg aggcctaggc ttttgcaaag atcgatcaag agacaggatg aggatcgttt    2640
cgcatgattg aacaagatgg attgcacgca ggttctccgg ccgcttgggt ggagaggcta    2700
ttcggctatg actgggcaca acagacaatc ggctgctctg atgccgccgt gttccggctg    2760
tcagcgcagg ggcgcccggt tctttttgtc aagaccgacc tgtccggtgc cctgaatgaa    2820
ctgcaagacg aggcagcgcg gctatcgtgg ctggccacga cgggcgttcc ttgcgcagct    2880
gtgctcgacg ttgtcactga agcgggaagg gactggctgc tattgggcga agtgccgggg    2940
caggatctcc tgtcatctca ccttgctcct gccgagaaag tatccatcat ggctgatgca    3000
atgcggcggc tgcatacgct tgatccggct acctgcccat tcgaccacca agcgaaacat    3060
cgcatcgagc gagcacgtac tcggatggaa gccggtcttg tcgatcagga tgatctggac    3120
gaagagcatc aggggctcgc gccagccgaa ctgttcgcca ggctcaaggc gagcatgccc    3180
gacggcgagg atctcgtcgt gacccatggc gatgcctgct tgccgaatat catggtggaa    3240
aatggccgct tttctggatt catcgactgt ggccggctgg gtgtggcgga ccgctatcag    3300
gacatagcgt tggctacccg tgatattgct gaagagcttg gcggcgaatg ggctgaccgc    3360
ttcctcgtgc tttacggtat cgccgctccc gattcgcagc gcatcgcctt ctatcgcctt    3420
cttgacgagt tcttctgagc gggactctgg ggttcgaaat gaccgaccaa gcgacgccca    3480
acctgccatc acgagatttc gattccaccg ccgccttcta tgaaaggttg gcttcggaa    3540 tcgtttccg ggacgccggc tggatgatcc tccagcgcgg ggatctcatg ctggagttct   3600
tcgcccaccc tagggggagg ctaactgaaa cacggaagga gacaataccg gaaggaaccc    3660
gcgctatgac ggcaataaaa agacagaata aaacgcacg tgttgggtcg tttgttcata     3720 aacgcgggt tcggtcccag ggctggcact ctgtcgatac cccaccgaga ccccattggg     3780
```

```
gccaatacgc ccgcgtttct tccttttccc cacccccaccc cccaagttcg ggtgaaggcc      3840
cagggctcgc agccaacgtc ggggcggcag gccctgccat agcctcaggt tactcatata      3900
tactttagat tgatttaaaa cttcattttt aatttaaaag gatctaggtg aagatccttt      3960
ttgataatct catgaccaaa atcccttaac gtgagttttc gttccactga gcgtcagacc      4020
ccgtagaaaa gatcaaagga tcttcttgag atccttttttt tctgcgcgta atctgctgct      4080
tgcaaacaaa aaaaccaccg ctaccagcgg tggtttgttt gccggatcaa gagctaccaa      4140 ctcttttttcc gaaggtaact ggcttcagca gagcgcagat accaaatact gtccttctag      4200
tgtagccgta gttaggccac cacttcaaga actctgtagc accgcctaca tacctcgctc      4260
tgctaatcct gttaccagtg gctgctgcca gtggcgataa gtcgtgtctt accgggttgg      4320
actcaagacg atagttaccg gataaggcgc agcggtcggg ctgaacgggg ggttcgtgca      4380
cacagcccag cttggagcga acgacctaca ccgaactgag atacctacag cgtgagctat      4440
gagaaagcgc cacgcttccc gaagggagaa aggcggacag gtatccggta agcggcaggg      4500
tcggaacagg agagcgcacg agggagcttc caggggggaaa cgcctggtat ctttatagtc      4560
ctgtcgggtt tcgccacctc tgacttgagc gtcgattttt gtgatgctcg tcagggggc      4620 ggagcctatg gaaaaacgcc agcaacgcgg ccttttttacg gttcctggcc ttttgctggc      4680
cttttgctca catgttcttt cctgcgttat cccctgattc tgtggataac cgtattaccg      4740
ccatgcat                                                              4748
```

<210> SEQ ID NO 5
<211> LENGTH: 4992
<212> TYPE: DNA
<213> ORGANISM: Artificial Sequence
<220> FEATURE:
<223> OTHER INFORMATION: Supplied by BD Biosciences Clonetech of Palo
      Alto, California

<400> SEQUENCE: 5

```
tagttattaa tagtaatcaa ttacggggtc attagttcat agcccatata tggagttccg       60
cgttacataa cttacggtaa atggcccgcc tggctgaccg cccaacgacc cccgcccatt      120
gacgtcaata atgacgtatg ttcccatagt aacgccaata gggactttcc attgacgtca      180
atgggtggag tatttacggt aaactgccca cttggcagta catcaagtgt atcatatgcc      240
aagtacgccc cctattgacg tcaatgacgg taaatggccc gcctggcatt atgcccagta      300
catgacctta tgggactttc ctacttggca gtacatctac gtattagtca tcgctattac      360
catggtgatg cggttttggc agtacatcaa tgggcgtgga tagcggtttg actcacgggg      420
atttccaagt ctccacccca ttgacgtcaa tgggagtttg ttttggcacc aaaatcaacg      480
ggactttcca aaatgtcgta acaactccgc cccattgacg caaatgggcg gtaggcgtgt      540
acggtgggag gtctatataa gcagagctgg tttagtgaac cgtcagatcc gctagcgcta      600
ccggtcgcca ccatggtgag caagggcgag gagctgttca ccggggtggt gcccatcctg      660
gtcgagctgg acggcgacgt aaacggccac aagttcagcg tgtccggcga gggcgagggc      720
gatgccacct acggcaagct gaccctgaag ttcatctgca ccaccggcaa gctgcccgtg      780 cccctggccca ccctcgtgac caccctgacc tacgcgtgc agtgcttcag ccgctacccc      840
gaccacatga gcagcacga cttcttcaag tccgccatgc ccgaaggcta cgtccaggag      900
cgcaccatct tcttcaagga cgacggcaac tacaagaccc gcgccgaggt gaagttcgag      960
ggcgacaccc tggtgaaccg catcgagctg aagggcatcg acttcaagga ggacggcaac     1020
```

-continued

```
atcctggggc acaagctgga gtacaactac aacagccaca acgtctatat catggccgac    1080
aagcagaaga acggcatcaa ggtgaacttc aagatccgcc acaacatcga ggacggcagc    1140
gtgcagctcg ccgaccacta ccagcagaac acccccatcg gcgacggccc cgtgctgctg    1200
cccgacaacc actacctgag cacccagtcc gccctgagca agacccccaa cgagaagcgc    1260
gatcacatgg tcctgctgga gttcgtgacc gccgccggga tcactctcgg catggacgag    1320
ctgtacaagt actcagatct cgagctcaag cttaccatgg ggggttctca tcatcatcat    1380
catcatggta tggctagcat gactggtgga cagcaaatgg gtcgggatct gtacgacgat    1440
gacgataagg ggactgctgc ggccaatgcg aacgacttct cgccaagcg caagagaact    1500
gcgcaggaga acaaggcgtc gaacgacgtc cctccagggt gtccctctcc aaacgtggct    1560
cctggggtgg gcgcggtgga gcagacccg cgcaaacgtc tgagatgagg atccagtgtg    1620
gtggaattct gcagatatcc agcacagtgg cggccgctcg agtctagata actgatcata    1680
atcagccata ccacatttgt agaggtttta cttgctttaa aaaacctccc acacctcccc    1740
ctgaacctga aacataaaat gaatgcaatt gttgttgtta acttgtttat tgcagcttat    1800
aatggttaca ataaagcaa tagcatcaca aatttcacaa ataaagcatt ttttttcactg    1860
cattctagtt gtggttttgtc caaactcatc aatgtatctt aacgcgtaaa ttgtaagcgt    1920
taatattttg ttaaaattcg cgttaaattt tgttaaatc agctcatttt ttaaccaata    1980
ggccgaaatc ggcaaaatcc cttataaatc aaaagaatag accgagatag ggttgagtgt    2040
tgttccagtt tggaacaaga gtccactatt aaagaacgtg gactccaacg tcaaagggcg    2100
aaaaaccgtc tatcagggcg atggcccact acgtgaacca tcaccctaat caagttttttt    2160
ggggtcgagg tgccgtaaag cactaaatcg gaaccctaaa gggagccccc gattttagagc    2220
ttgacgggga agccggcga acgtggcgag aaaggaaggg aagaaagcga aggagcggg    2280
cgctagggcg ctggcaagtg tagcggtcac gctgcgcgta accaccacac cgccgcgct    2340
taatgcgccg ctacagggcg cgtcaggtgg cacttttcgg ggaaatgtgc gcggaacccc    2400
tatttgttta ttttttctaaa tacattcaaa tatgtatccg ctcatgagac aataaccctg    2460
ataaatgctt caataatatt gaaaaaggaa gagtcctgag gcggaaagaa ccagctgtgg    2520
aatgtgtgtc agttagggtg tggaaagtcc ccaggctccc cagcaggcag aagtatgcaa    2580
agcatgcatc tcaattagtc agcaaccagg tgtggaaagt ccccaggctc ccagcaggc    2640
agaagtatgc aaagcatgca tctcaattag tcagcaacca tagtcccgcc cctaactccg    2700
cccatcccgc ccctaactcc gcccagttcc gcccattctc cgccccatgg ctgactaatt    2760
ttttttatt atgcagaggc cgaggccgcc tcggcctctg agctattcca gaagtagtga    2820
ggaggctttt ttggaggcct aggcttttgc aaagatcgat caagagacag gatgaggatc    2880
gtttcgcatg attgaacaag atggattgca cgcaggttct ccggccgctt gggtggagag    2940
gctattcggc tatgactggg cacaacagac aatcggctgc tctgatgccg ccgtgttccg    3000
gctgtcagcg caggggcgcc cggttctttt tgtcaagacc gacctgtccg gtgccctgaa    3060
tgaactgcaa gacgaggcag cgcggctatc gtggctggcc acgacgggcg ttccttgcgc    3120
agctgtgctc gacgttgtca ctgaagcggg aagggactgg ctgctattgg gcgaagtgcc    3180
ggggcaggat ctcctgtcat ctcaccttgc tcctgccgag aaagtatcca tcatggctga    3240
tgcaatgcgg cggctgcata cgcttgatcc ggctacctgc ccattcgacc accaagcgaa    3300
acatcgcatc gagcgagcac gtactcggat ggaagccggt cttgtcgatc aggatgatct    3360
```

-continued

```
ggacgaagag catcaggggc tcgcgccagc cgaactgttc gccaggctca aggcgagcat  3420
gcccgacggc gaggatctcg tcgtgaccca tggcgatgcc tgcttgccga atatcatggt  3480
ggaaaatggc cgcttttctg gattcatcga ctgtggccgg ctgggtgtgg cggaccgcta  3540
tcaggacata gcgttggcta cccgtgatat tgctgaagag cttggcggcg aatgggctga  3600
ccgcttcctc gtgctttacg gtatcgccgc tcccgattcg cagcgcatcg ccttctatcg  3660
ccttcttgac gagttcttct gagcgggact ctggggttcg aaatgaccga ccaagcgacg  3720
cccaacctgc catcacgaga tttcgattcc accgccgcct tctatgaaag gttgggcttc  3780
ggaatcgttt tccgggacgc cggctggatg atcctccagc gcgggatct catgctggag  3840 ttcttcgccc accctagggg gaggctaact gaaacacgga aggagacaat accggaagga  3900
acccgcgcta tgacggcaat aaaaagacag aataaaacgc acggtgttgg gtcgtttgtt  3960
cataaacgcg gggttcggtc ccagggctgg cactctgtcg ataccccacc gagaccccat  4020
tggggccaat acgcccgcgt ttcttccttt tccccacccc acccccaag ttcgggtgaa  4080 ggcccagggc tcgcagccaa cgtcggggcg gcaggccctg ccatagcctc aggttactca  4140
tatatacttt agattgattt aaaacttcat ttttaattta aaaggatcta ggtgaagatc  4200 cttttttgata atctcatgac caaaatccct taacgtgagt tttcgttcca ctgagcgtca  4260
gaccccgtag aaaagatcaa aggatcttct tgagatcctt ttttctgcg cgtaatctgc  4320 tgcttgcaaa caaaaaaacc accgctacca gcggtggttt gtttgccgga tcaagagcta  4380
ccaactcttt ttccgaaggt aactggcttc agcagagcgc agataccaaa tactgtcctt  4440
ctagtgtagc cgtagttagg ccaccacttc aagaactctg tagcaccgcc tacatacctc  4500
gctctgctaa tcctgttacc agtggctgct gccagtggcg ataagtcgtg tcttaccggg  4560
ttggactcaa gacgatagtt accggataag gcgcagcggt cgggctgaac ggggggttcg  4620
tgcacacagc ccagcttgga gcgaacgacc tacaccgaac tgagatacct acagcgtgag  4680
ctatgagaaa gcgccacgct tcccgaaggg agaaaggcgg acaggtatcc ggtaagcggc  4740
agggtcggaa caggagagcg cacgagggag cttccagggg gaaacgcctg gtatctttat  4800
agtcctgtcg ggtttcgcca cctctgactt gagcgtcgat ttttgtgatg ctcgtcaggg  4860
gggcggagcc tatggaaaaa cgccagcaac gcggcctttt tacggttcct ggccttttgc  4920
tggccttttg ctcacatgtt ctttcctgcg ttatcccctg attctgtgga taaccgtatt  4980
accgccatgc at                                                      4992
```

NANOPARTICLE ENCAPSULATION SYSTEM AND METHOD

CROSS-REFERENCE TO RELATED APPLICATION(S)

The present application claims priority from application Ser. No. 60/185,282 filed on Feb. 28, 2000 entitled "NANOPARTICLE ENCAPSULATION SYSTEM AND METHOD" by Gretchen M. Unger.

BACKGROUND OF THE INVENTION

The present invention generally relates to a field of controlled-release delivery systems for macromolecules, particularly those for nucleic acids and gene therapy. More specifically, the present invention relates to nanocapsules having a diameter of less than about 50 nanometers, in which a bioactive component is located in a core of the nanocapsule, and to methods of forming these nanocapsules.

Over the past several decades, active and extensive research into the use of nanoparticles in the delivery of bioactive agents has generated a number of approaches in the preparation of nanoparticles. These approaches typically include the use of heat, high pressure homogenization, or high intensity ultrasound sonication to prepare nanoparticles having a diameter of more than 100 nanometers, or high amounts of solvents or oils, cytotoxic chemicals, such as cross-linking agents, adjuvants, catalysts or any combination of any of these, to prepare nanoparticles having a diameter of less than 100 nanometers. Furthermore, these approaches are challenging due to a number of variables.

For example, when organic solvents are included in the manufacturing process for nanoparticles, the organic solvent may denature the bioactive agent which reduces most, if not all, efficacy of the bioactive agent. In fact, denaturation of the bioactive agent may promote a toxic response upon administration of the nanoparticle, to a human subject, for example.

In addition, when an organic solvent is used to prepare nanoparticles, the organic solvent or solvent soluble polymer may undergo degradation to form a low pH environment that destroys the efficacy of the bioactive agent. Therefore, organic solvents may generally denature the bioactive agent during or after preparation of a nanoparticle.

As a result, organic solvents are typically removed during the manufacturing process of nanoparticles. However, inclusion of one or more organic solvent removal techniques generally increases the costs and complexity of forming nanoparticles.

The incorporation of high pressure homogenization or high intensity ultrasound sonication to prepare nanoparticles typically results in entangling or embedding the bioactive agent in a polymeric matrix of the nanoparticle. Entangling or embedding the bioactive agent in the polymeric matrix may also denature the bioactive agent to thereby reduce the efficacy of the bioactive agent.

Entangling or embedding the bioactive agent in the polymeric matrix of the nanoparticle may also reduce the efficacy of the bioactive agent by permitting premature release of the bioactive agent prior to reaching a target cell. Premature release of the bioactive agent typically promotes cytotoxicity or cell death during administration of the nanoparticle.

Furthermore, nanoparticles that reach the target cell are typically transported into the target cell via endosomal regulated pathways that results in lysosomal degradation of the bioactive agent and the nanoparticle. Therefore, functional activity of the bioactive agent inside the target cell may not occur since the bioactive agent and the nanoparticle undergoes degradation. As used herein, the term "functional activity" refers to an ability of a bioactive agent to function within a target cell for purposes of providing a therapeutic effect on the target cell.

Additionally, high pressure homogenization or high intensity ultrasound sonication techniques often require complex and expensive equipment that generally increases costs in preparing nanoparticles. Therefore, an urgent need exists to prepare nanoparticles without the use of cytotoxic chemicals like organic solvents or the use of complex and expensive equipment. Furthermore, an urgent need exists to prepare nanoparticles that do not entangle nor embed the bioactive agent in the nanoparticle so that cytotoxic responses are minimized. Additionally, an urgent need exists to develop a nanoparticle that may be transported into a target cell where the bioactive agent is released to accomplish therapeutic delivery of the bioactive agent.

BRIEF SUMMARY OF THE INVENTION

The present invention generally relates to nanocapsules and methods of preparing these nanocapsules. The present invention includes a method of forming a surfactant micelle and dispersing the surfactant micelle into an aqueous composition having a hydrophilic polymer to form a stabilized dispersion of surfactant micelles. The method further includes mechanically forming droplets of the stabilized dispersion of surfactant micelles, precipitating the hydrophilic polymer to form precipitated nanocapsules, incubating the nanocapsules to reduce a diameter of the nanocapsules, and filtering or centrifuging the nanocapsules.

DETAILED DESCRIPTION

The present invention generally relates to nanocapsules having a diameter of less than about 50 nanometers (nm). The present invention also relates to a method of preparing these nanocapsules. According to the method of the present invention, a nanocapsule is formed by partitioning a bioactive component within a core of surfactant molecules, and surrounding the surfactant molecules with a biocompatible polymer shell.

Figure 1:
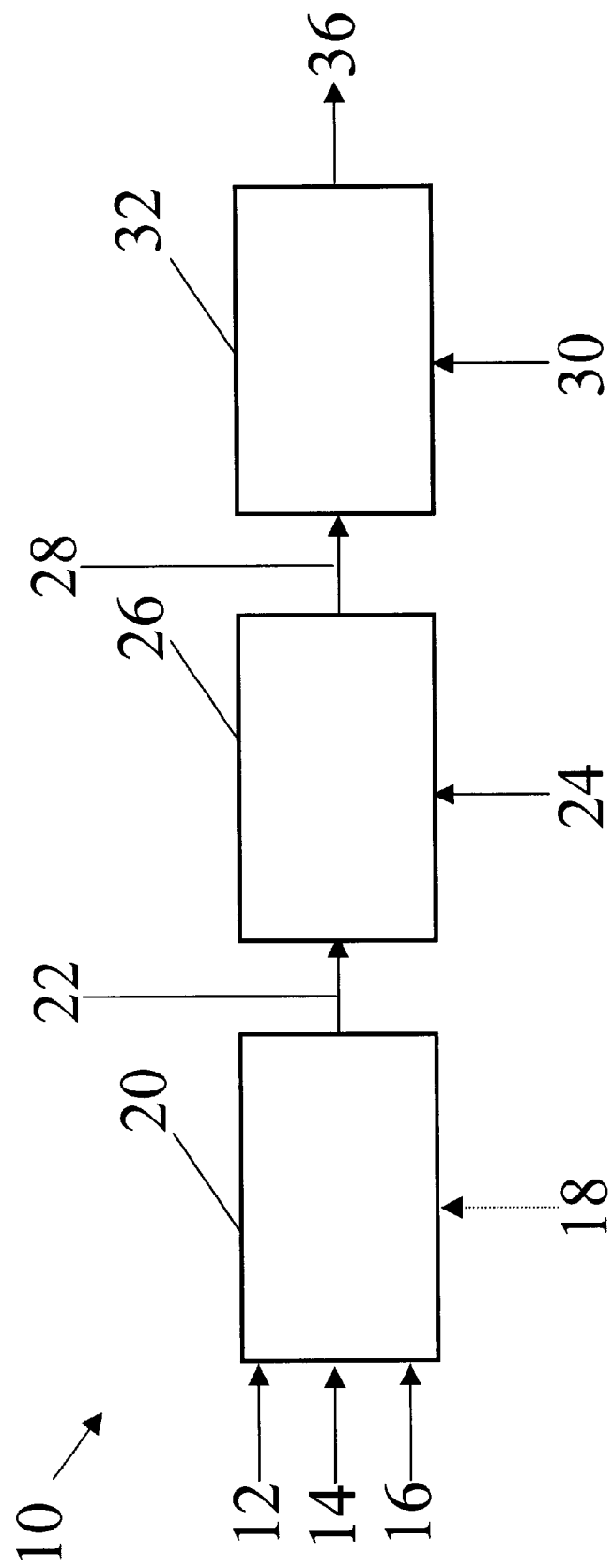
FIG. 1 is a schematic of a method of the present invention for preparing nanocapsules.

A method for producing the nanocapsule is generally depicted at 10 in FIG. 1. In the method 10, a bioactive component 12 is homogeneously dispersed into a first aqueous composition 14 to form a hydrophilic composition (not shown). Next, a surfactant composition 16, including a surfactant component (not shown) that contains a plurality of surfactant molecules, and an optional biocompatible oil component 18, are introduced into a first dispersing apparatus 20 along with the hydrophilic composition. The surfactant composition 16 is subjected to conditions in the first dispersing apparatus 20 that initiate at least partial adsorption of the surfactant molecules onto a surface of the bioactive component 12.

Partial adsorption of surfactant molecules onto the surface of the bioactive component 12 initiates partitioning of the bioactive component 12 into a core of a shell formed from the surfactant molecules in the first aqueous composition 14. Adsorption of the surfactant molecules onto the surface of the bioactive component 12 may proceed until an entire surface of the bioactive component 12 is covered by the surfactant molecules to complete partitioning of the bioactive component 12 into the core of surfactant molecules and form a surfactant micelle 22.

Next, a biocompatible polymer component 24 is added to the surfactant micelle 22 to stabilize the surfactant micelle 22 located in the first aqueous composition 14. Preferably, the biocompatible polymer component 24 surrounds the surfactant micelle 22 in a stabilizing apparatus 26 to form a stabilized surfactant micelle 28.

After stabilization, the stabilized surfactant micelle 28 is transferred from the stabilizing apparatus 26 into a second aqueous composition 30 located in a second dispersing apparatus 32. Preferably, the second aqueous composition 30 includes a solute (not shown) that is capable of precipitating the biocompatible polymer component 24 that coats the stabilized surfactant micelle 28. After precipitating the biocompatible polymer component 24 of the stabilized surfactant micelle 28, dispersed, optionally atomized precipitated nanocapsules 36, hereinafter referred to as nanocapsules 36, are formed.

It has been discovered that dispersing a surfactant composition, that includes a surfactant component having a hydrophile-lipophile-balance (HLB) value of less than about 6.0 units, into an aqueous composition that contains a bioactive component forms surfactant micelles that surround the bioactive component. It has further been discovered that stabilizing the surfactant micelles by adding a biocompatible polymer coats the surfactant micelles to form nanocapsules having a diameter of less than about 50 nm.

As used herein, the term "nanoparticle" refers to a particle having a matrix-type structure with a size of less than about 1,000 nanometers. When the nanoparticle includes a bioactive component, the bioactive component is entangled or embedded in the matrix-type structure of the nanoparticle.

The term "nanosphere", as used herein, refers to a particle having a solid spherical-type structure with a size of less than about 1,000 nanometers. When the nanosphere includes a bioactive component, the bioactive component is adsorbed onto the surface of the nanosphere or embedded in the nanosphere.

Similarly, the term "nanocore", as used herein, refers to a particle having a solid core with a size of less than about 1,000 nanometers. When the nanocore includes a bioactive component, the bioactive component is entangled in the nanocore.

As used herein, the term "nanocapsule" refers to a particle having a hollow core that is surrounded by a shell, such that the particle has a size of less than about 1,000 nanometers. When a nanocapsule includes a bioactive component, the bioactive component is located in the core that is surrounded by the shell of the nanocapsule. The term "nanocapsule" is not meant to encompass, and generally does not include, a particle having a size of less than about 1,000 nanometers, in which a bioactive component is entangled or embedded in the matrix of the nanocapsule or adsorbed onto the surrounding shell of the nanocapsule.

The bioactive component 12 may be included into the first aqueous composition 14 as a liquid, vapor or in granular form. The form of the bioactive component 12 that is selected preferably permits the bioactive component 12 to (1) remain stable prior to dissolving or dispersing into the first aqueous composition 14, (2) be homogeneously dispersed into the first aqueous composition 14, (3) be optionally condensed to reduce a size of the bioactive component 12, (4) be partitioned into the core of the surfactant micelles 22, (5) be released upon degradation of the biocompatible polymer shell 24 of the nanocapsule 36, and (6) be functionally active upon release from the nanocapsule 36.

The bioactive component 12 may be characterized as "hydrophilic" or "hydrophobic". As used herein, the term "hydrophilic" and "hydrophilicity" refers to an ability of a molecule to adsorb water or form one or more hydrogen-bond(s) with water. All references to "hydrophilic" are also understood as encompassing any portion of the molecule that is capable of adsorbing water or forming one or more hydrogen-bond(s) with water. As used herein, the term "hydrophobic" and "hydrophobicity" refers to an ability of a molecule to not adsorb water nor form one or more hydrogen-bond(s) with water. All references to "hydrophobic" are also understood as encompassing any portion of the molecule that is not capable of adsorbing water nor forming one or more hydrogen-bond(s) with water.

When the bioactive component 12 is a hydrophilic bioactive component, the hydrophilic bioactive component may be directly added to the first aqueous composition 14. As an alternative, the hydrophilic bioactive component 12 may be optionally dissolved or dispersed in one or more solvents, such as water, a nonpolar solvent, a polar solvent, or any combination of any of these.

As used herein, the term "nonpolar solvent" refers to a solvent that does not have a permanent electric dipole moment, and therefore has no ability for an intramolecular association with a polar solvent. Additionally, a nonpolar solvent may be characterized as a solvent that includes molecules having a dielectric constant of less than about 20 units. Similarly, the term "immiscible", as used herein, refers to an inability of two or more substances, such as two or more liquids, solids, vapors, or any combination of any of these, to form an intramolecular association with another substance. Some non-exhaustive examples of nonpolar solvents may be found in Perry's Chemical Engineer's Handbook, Sixth Edition, which is incorporated herein by reference.

As used herein, the term "polar solvent" refers to a solvent that has a permanent electrical dipole moment, and therefore has an ability to form an intramolecular association with another polar substance, such as a liquid, a solid, a vapor or any combination of any of these. Additionally, a polar solvent may be characterized as a solvent that includes molecules having a dielectric constant of more than about 20 units. Likewise, the term "miscible", as used herein, refers to an ability of two or more substances to form an intramolecular association with each other. Some non-exhaustive examples of polar solvents may be found in Perry's Chemical Engineer's Handbook, Sixth Edition, which has been incorporated herein by reference.

When the bioactive component 12 is a hydrophobic bioactive component, the hydrophobic bioactive component may be dispersed or dissolved in a solvent that is capable of dispersing or dissolving the hydrophobic molecule, such as the above-mentioned water, a nonpolar solvent, a polar solvent, or any combination of any of these. Preferably, when the bioactive component 12 is a hydrophobic bioactive component 12, the hydrophobic bioactive component 12 is dissolved or dispersed in a water-miscible solvent, such as, acetone, acetonitrile, ethanol, dimethyl acetamide (DMA), tetrahydrofuran (THF), dioxane, dimethylsulfoxide (DMSO), and dimethylformamide (DMF). Other suitable non-exhaustive examples of water-miscible solvents may be found in Perry's Chemical Engineer's Handbook, Sixth Edition, which has been incorporated herein by reference.

As noted, the bioactive component 12 may be optionally condensed in the first aqueous composition 14 prior to forming the surfactant micelle 16. For example, when the bioactive component is a polynucleotide, the polynucleotide may be condensed using a DNA-condensing agent. As used herein, a "DNA-Condensing Agent" is a molecule that facilitates condensation or a size reduction of DNA.

While condensation of the bioactive component 12 is not critical to the present invention, condensation of the bioactive component 12 maybe practiced to reduce the size of the bioactive component 12. Condensation of the bioactive component 12 generally reduces the size of the bioactive component 12 prior to partitioning into the core of the surfactant micelle 16. Reducing the size of the bioactive component 12 may permit maximum incorporation of the bioactive component 12 into the surfactant micelle 22 or may assist a reduction in the overall size of the nanocapsule 36. Increasing the amount of the bioactive component 12 that may be included as part of the nanocapsule 36 permits incorporation of macromolecules having a large number of monomers, such as a large number of base pairs or amino acids, for example. Some non-exhaustive examples of condensing agents have been reviewed in Rolland, A. P. (1998). *Crit. Rev. Therapeutic Drug. Carr. Syst.* 15:143–198, and is incorporated herein by reference.

The bioactive component 12 may further include additional components that are compatible with, and that do not interfere with solvation or dispersion of the bioactive component 12. Some non-exhaustive examples of additional components that may be added to the bioactive component 12 include a DNA-associating moiety, which refers to a molecule, or portions thereof, that interact in a non-covalent fashion with nucleic acids. DNA-associating moieties may include, but are not limited to, a major-and minor-groove binder, a DNA intercalator, a polycation, a DNA-masking component, a membrane-permeabilizing component, a subcellular-localization component, or the like. Major- and minor-groove binders, as used herein, are molecules thought to interact with DNA by associating with the major or minor groove of double-stranded DNA.

Similarly, the term "DNA intercalator" as used herein, refers to a planar molecule or planar portion of a molecule thought to intercalate into DNA by inserting themselves between, and parallel to, a nucleotide base pair. As used herein, a "polycation" is thought to associate with the negative charges on the DNA backbone. The DNA-associating moiety may be covalently linked through a "reactive group" to a functional component of this invention. The reactive group is easily reacted with a nucleophile on the functional component. Some non-exhaustive examples of reactive groups (with their corresponding reactive nucleophiles) include, but are not limited to N-hydroxysuccinimide (e.g., amine), maleimide and maleimidophenyl (e.g., sulfhydryl), pyridyl disulfide (e.g., sulfhydryl), hydrazide (e.g., carbohydrate), and phenylglyoxal (e.g., arginine).

The term "DNA-masking component", as used herein, refers to a molecule capable of masking all or part of a polynucleotide following release from a nanocapsule to increase its circulatory half-life by inhibiting attack by degrading reagents, such as nucleases, present in the circulation and/or interfering with uptake by the reticuloendothelial system. Similarly, the term "membrane-permeabilizing component", as used herein, refers to any component that aids in the passage of a polynucleotide or encapsulated polynucleotide across a membrane. Therefore, "membrane permeabilizing component" encompasses in part a charge-neutralizing component, usually a polycation, that neutralizes the large negative charge on a polynucleotide, and enables the polynucleotide to traverse the hydrophobic interior of a membrane.

Many charge-neutralizing components can act as membrane-permeabilizers. Membrane-permeabilization may also arise from amphipathic molecules. A "membrane permeabilizer", as used herein, is a molecule that can assist a normally impermeable molecule to traverse a cellular membrane and gain entrance to the cytoplasm of the cell. The membrane permeabilizer may be a peptide, bile salt, glycolipid, phospholipid or detergent molecule. Membrane permeabilizers often have amphipathic properties such that one portion is hydrophobic and another is hydrophilic, permitting them to interact with membranes.

The term "subcellular-localization component", as used herein, refers to a molecule capable of recognizing a subcellular component in a targeted cell. Recognized subcellular components include the nucleus, ribosomes, mitochondria, and chloroplasts. Particular subcellular-localization components include the "nuclear-localization components" that aid in carrying molecules into the nucleus and are known to include the nuclear localization peptides and amino acid sequences.

The bioactive component 12 may be included at an amount that is therapeutically effective to transform a plurality of cells, such as in vitro, in vivo or ex vivo cells. As used herein, "transform" refers to a presence and/or functional activity of the bioactive component in the plurality of cells after exposing the nanocapsules to the plurality of cells.

Furthermore, those of ordinary skill in the art will recognize that the amount of the bioactive component 12 may vary depending upon the bioactive component 12, the temperature, pH, osmolarity, any solutes, any additional component or optional solvents present in the first aqueous composition 14, the surfactant composition 16, a type or an amount of the surfactant micelle 22, the biocompatible polymer component 24, any desired characteristics of the stabilized surfactant micelle 28, any desired characteristics of the nanocapsules 36, or any combination of any of these.

The bioactive component 12 of the nanocapsule 36 may be supplied as an individual macromolecule or supplied in various prepared mixtures of two or more macromolecules that are subsequently combined to form the bioactive component 12. Some non-exhaustive examples of hydrophilic macromolecules that ay be suitable for inclusion as part of the bioactive component 12 include, but are not limited to polynucleotides, polypeptides, genetic material, peptide nucleic acids, aptamers, carbohydrates, mini-chromosomes, molecular polymers, aggregates or associations of an inorganic or organic nature, genes, any other hydrophilic macromolecule or any combination of any of these.

Some non-exhaustive examples of hydrophobic macromolecules that may be included part of the bioactive component 12 include, but are not limited to, adrenergic, adrenocortical steroid, adrenocortical suppressant, aldosterone antagonist, and anabolic agents; analeptic, analgesic, anesthetic, anorectic, and anti-acne agents; anti-adrenergic, anti-allergic, anti-amebic, anti-anemic, and anti-anginal agents; anti-arthritic, anti-asthmatic, anti-atherosclerotic, antibacterial, and anticholinergic agents; anticoagulant, anticonvulsant, antidepressant, antidiabetic, and antidiarrheal agents; antidiuretic, anti-emetic, anti-epileptic, antifibrinolytic, and antifungal agent; antihemorrhagic, inflammatory, antimicrobial, antimigraine, and antimiotic agents; antimycotic, antinauseant, antineoplastic, antineutropenic, and antiparasitic agents; antiproliferative, antipsychotic, antirheumatic, antiseborrheic, and antisecretory agents; antispasmodic, antithrombotic, anti-ulcerative, antiviral, and appetite suppressant agents; blood glucose regulator, bone resorption inhibitor, bronchodilator, cardiovascular, and cholinergic agents; fluorescent, free oxygen radical scavenger, gastrointestinal motility effector, glucocorticoid, and hair growth stimulant agent; hemostatic, histamine H2 receptor antagonists; hormone; hypocholesterolemic, and hypoglycemic agents; hypolipidemic, hypotensive, and imaging agents, immunizing and agonist agents; mood regulators, mucolytic, mydriatic, or nasal decongestant; neuromuscular blocking agents; neuroprotective, NMDA antagonist, non-hormonal sterol derivative, plasminogen activator, and platelet activating factor antagonist agent; platelet aggregation inhibitor, psychotropic, radioactive, scabicide, and sclerosing agents; sedative, sedative-hypnotic, selective adenosine A1 antagonist, serotonin antagonist, and serotonin inhibitor agent; serotonin receptor antagonist, steroid, thyroid hormone, thyroid hormone, and thyroid inhibitor agent; thyromimetic, tranquilizer, amyotrophic lateral sclerosis, cerebral ischemia, and Paget's disease agent; unstable angina, vasoconstrictor, vasodilator, wound healing, and xanthine oxidase inhibitor agent; immunological agents, antigens from pathogens, such as viruses, bacteria, fungi and parasites, optionally in the form of whole inactivated organisms, peptides, proteins, glycoproteins, carbohydrates, or combinations thereof, any examples of pharmacological or immunological agents that fall within the above-mentioned categories and that have been approved for human use that may be found in the published literature, any other hydrophobic bioactive component, or any combination of any of these.

As used herein, the term "polypeptide" refers to a polymer of amino acids not limited by the number of amino acids. It is also to be understood that the term "polypeptide" is meant to encompass an oligopeptide, a peptide, or a protein, for example.

As used herein, the term "polynucleotide" refers to RNA or DNA sequences of more than 1 nucleotide in either single chain, duplex or multiple chain form. The term "polynucleotide" is also meant to encompass polydeoxyribonucleotides containing 2'-deoxy-D-ribose or modified forms thereof, RNA and any other type of polynucleotide which is an N-glycoside or C-glycoside of a purine or pyrimidine base, or modified purine or pyrimidine base or basic nucleotide. The polynucleotide may encode promoter regions, operator regions, structural regions, termination regions, combinations thereof or any other genetically relevant material. Similarly, the term "genetic" as used herein, refers to any material capable of modifying gene expression.

The first aqueous composition 14 may be included in the method of the present invention as a gel, liquid, or in vapor form. The form of the first queous composition 14 that is selected preferably permits the first aqueous composition 14 to (1) remain stable prior to dissolving or dispersing the bioactive component, the surfactant composition 16, the surfactant micelle 22, or optionally the stabilizer surfactant micelle 28, (2) homogeneously disperse the bioactive component 12, the surfactant composition 16, the surfactant micelle 22, or optionally the stabilizer surfactant 28, (3) function as a continuous phase in an oil-in-water emulsion, (4) not interfere with, or mask the functional activity of the bioactive component 12, and (5) not modify or degrade the bioactive component 12, the surfactant composition 16, the surfactant micelle 22, or optionally the stabilized surfactant micelle 28.

The first aqueous composition 14 may include only water, or may optionally include additional solutes or solvents that do not interfere with the method of forming the nanocapsules 36 nor mask the functional activity of the bioactive component 12. Furthermore, those of ordinary skill in the art will recognize that an amount of the first aqueous composition 14 used to prepare the nanocapsules 36 may vary depending upon the bioactive component 12, the surfactant composition 16, the temperature, pH, osmolarity, optional solutes or optional solvents, the surfactant micelle 22, the biocompatible polymer component 24, any desired characteristics of the stabilized surfactant micelle 28 or the nanocapsules 36.

The bioactive component 12 may be added to the first aqueous composition 14 or the first aqueous composition 14 may be added to the bioactive component 12. While the order of addition of the bioactive component 12 and the first aqueous composition 14 is not critical to the present invention, the hydrophilic composition (not shown) that is formed when the bioactive component 12 is dissolved or dispersed in the first aqueous composition 14 is preferably capable of maintaining a homogeneous solution or dispersion in the hydrophilic composition.

The first aqueous composition 14 may be supplied as an individual component or supplied in various prepared mixtures of two or more components that are subsequently combined to form the first aqueous composition 14. Some non-exhaustive examples of the first aqueous composition 14 include, but are not limited to, the above-mentioned water, nonpolar solvents, polar solvents, or any combination of any of these. Preferably, water is the first aqueous composition 14.

The surfactant composition 16 may be introduced into the bioactive component 12, the first aqueous composition 14, the hydrophilic composition as a liquid, vapor or in granular form. The form of the surfactant composition 16 that is selected preferably permits the surfactant composition 16 to (1) remain stable prior to introducing into the bioactive component 12, the first aqueous composition 14, or the hydrophilic composition, (2) be homogeneously dispersed into the bioactive component 12, the first aqueous composition 14, or the hydrophilic composition, (3) form a micellar structure, (4) be adsorbed onto a surface of the bioactive component 12, the first aqueous composition 14, the hydrophilic composition (5) displace the first aqueous composition that is located on the surface of the bioactive component 12, (6) partition the bioactive component 12 or the hydrophilic composition into a core of the micellar structure to form the surfactant micelle 22, and (7) provide a thermodynamic driving force that is effective to reduce a size of the bioactive component 12, surfactant micelle 22, the stabilized surfactant 28 or the nanocapsule 36.

As used herein, a "surfactant" refers to any molecule containing a polar portion that thermodynamically prefers to be solvated by a polar solvent, and a hydrocarbon portion that thermodynamically prefers to be solvated by a nonpolar solvent. The term "surfactant" is also meant to encompass anionic, cationic, or non-ionic surfactants. As used herein, the term "anionic surfactant" refers to a surfactant with a polar portion that ionizes to form an anion in aqueous solution. Similarly, a "cationic surfactant" refers to a surfactant having a cationic polar portion that ionizes to form a cation in aqueous solution. Likewise, a "non-ionic" surfactant refers to a surfactant having a polar portion that does not ionize in aqueous solution.

While not wanting to be bound to theory, it is generally believed that a surfactant refers to a molecule that is effective to reduce a surface or an interfacial tension between a first substance dispersed in a second substance such that the first substance is solvated and any molecular groups of the first substance are dispersed. Typically, a hydrodynamic diameter of the first substance increases after addition of the surfactant. Nonetheless, the surfactant composition 16 is believed to be effective to reduce the size or diameter of the surfactant micelles 22 in the first aqueous composition 14, to thereby reduce the size of the nanocapsule 36 when practicing the present invention.

The surfactant composition 16 may include the surfactant component only (not shown), or may optionally include the biocompatible oil component 18. The surfactant component may be characterized on the HLB (Hydrophile-Lipophile Balance) scale that ranges from less than about 1 to more than about 13 units.

A surfactant component having an HLB value of less than about 6.0 units may be described as being poorly, or not dispersable in an aqueous or water-based composition. In addition, a surfactant component having an HLB value of less than about 6.0 units may be characterized as a hydrophobic or non-ionic surfactant. A surfactant component having an HLB value of more than about 7.0 units may be described as being capable of forming a milky to translucent to clear dispersion when the surfactant having an HLB value of more than about 7.0 units is dispersed in an aqueous or water-based composition.

Preferably, the surfactant component of the surfactant composition 16 has an HLB value of less than about 6.0 units when practicing the method of the present invention. Still more preferably the surfactant component of the surfactant composition 16 has an HLB value of less than about 5.0 units to facilitate preparation of nanocapsules having a diameter of less than about 50 nm.

The surfactant component may also be characterized in terms of a critical micelle concentration (CMC) value. Preferably, the surfactant component of the surfactant composition 16 has a CMC value of less than about 300 micromolars ($\mu$m). Still more preferably, the surfactant component has a CMC value of less than about 200 $\mu$m.

While not wanting to be bound to theory, it is believed that the surfactant component of the surfactant composition 16 adsorbs onto the surface of the bioactive component 12 when introduced into the first aqueous composition 14 to minimize exposure of a surface of the hydrophobic surfactant component to a thermodynamically unfavorable environment created by the first aqueous composition 14. Therefore, the surfactant component adsorbs onto the surface of the bioactive component to reduce the surface area of the surfactant component that may be exposed to the first aqueous composition 14. Adsorption of the surfactant component onto the bioactive component 12 is believed to facilitate the size reduction of the bioactive component 12 and/or the surfactant micelle 22.

The surfactant component of the surfactant composition 16 may be supplied as individual surfactants or supplied in various prepared mixtures of two or more surfactants that are subsequently combined to form the surfactant composition 16. Some non-exhaustive examples of suitable surfactants having an HLB value of less than about 6.0 units or a CMC value of less than about 200 $\mu$m be listed in *Dermatological Formulations* (Barry, B., Marcel Dekker, (1983)), or in *Percutaneous absorption: drug, cosmetics, mechanisms, methodology*, $3^{rd}$ ed., Bronough, R. ed., 1999, or the *Handbook of Industrial Surfactants* (Ash, M, Ed., Gower Pub. (1993), which are incorporated herein by reference. As an example, the surfactant component maybe 2,4,7,9-tetramethyl-5-decyn-4,7-diol(TM-diol), blends of 2,4,7,9-tetramethyl-5-decyn-4,7-diol(TM-diol), molecules having one or more acetylenic diol groups, cetyl alcohol or any combination of any of these.

The optional biocompatible oil component 18 of the surfactant composition 16 may be combined with the surfactant component as a liquid, vapor or in granular form. The form of the optional biocompatible oil component 18 that is selected preferably permits the optional biocompatible oil component 18 to (1) remain stable prior to introduction into the surfactant composition 16, (2) be homogeneously blended into the surfactant composition 16, (3) dissolve or disperse the surfactant component, and (4) increase the hydrophobicity of the surfactant composition 16, and therefore, the degree to which the size of the bioactive component 12, the surfactant micelle 22, the stabilizer surfactant micelle 28, or the nanocapsule 36 may be reduced when practicing the present invention.

Preferably, the concentration of the optional biocompatible oil component 18 in the surfactant composition 16 ranges from about $10^{-7}$ weight percent to about 10 weight percent, based upon a total volume of the stabilized surfactant micelles 28. Concentrations of the optional biocompatible oil component 18 higher than about 10 weight percent, based upon the total volume of the stabilized surfactant micelles 28, may be less desirable because such higher concentrations increase a phase volume of the biocompatible oil, and consequently may cause difficulties in preparing, dispersing and/or handling the surfactant micelles 22, the stabilized surfactant micelles 28 or the nanocapsules 36. Concentrations of the optional biocompatible oil component lower than about $10^{-7}$ weight percent in the surfactant composition 16 may be less preferred, because such lower concentrations would not be effective to solvate the surfactant component, or increase the hydrophobicity of the surfactant composition 16, and may ultimately increase the diameter of the nanocapsules 36.

The optional biocompatible oil component 18 of the surfactant composition 16 may be supplied as an individual biocompatible oil or supplied in various prepared mixtures of two or more biocompatible oils that are subsequently combined to form the optional biocompatible oil component 18. Some non-exhaustive examples of suitable biocompatible oils that may be included as part of the biocompatible oil component 18 maybe found in *Dermatological Formulations* (Barry, B., Marcel Dekker, (1983)), or in *Percutaneous absorption: drug, cosmetics, mechanisms, methodology*, $3^{rd}$ ed., Bronough, R. ed, 1999, or in the *Handbook of industrial Surfactants* (Ash, M, Ed., Gower Pub. (1993), which have been incorporated herein by reference. Preferably, food or USP grade oils, such as DMSO, DMF, castor oil, or any combination thereof, are used to practice the present method.

The surfactant composition 16 may be included at an amount that is effective to form the micellar structure that partitions the bioactive component 12, the first aqueous composition 14 or the hydrophilic composition into the core of the micellar structure when forming the surfactant micelle 22. Still more preferably, the surfactant composition 16 is included at an amount that is effective to provide a maximum thermodynamic driving force that minimizes the size of the bioactive component 12, the surfactant micelle 22, and ultimately, the size of the nanocapsule 36 when practicing the present invention.

Furthermore, those of ordinary skill in the art will recognize that the amount of the surfactant composition 16 may be varied based upon the bioactive component 12, the first aqueous composition 14, a ratio of the surfactant component to the optional biocompatible oil 18, any desired characteristics of the surfactant micelles 22, the stabilized surfactant micelles 28 or the nanocapsules 36. For example, a surfactant composition containing a surfactant component having an HLB value of about 6.0 units mixed with a nonpolar biocompatible oil like castor oil, may provide the same degree of a thermodynamic driving force as a second surfactant composition containing a surfactant component of about 4.0 units mixed with DMSO.

The amount of the surfactant composition 16 may range up to about 0.5 weight percent, based upon a total volume of the stabilized surfactant micelles 28. Still more preferably, the amount of the surfactant composition 16 is less than about 0.25 weight percent, based upon the total volume of the stabilized surfactant micelles 28. Most preferably, the surfactant composition 16 is present at an amount of less than about 0.05 weight percent, based upon the total volume of the stabilized surfactant micelles 28. As one non-exhaustive example, the surfactant composition 16 may be added to the total volume of the hydrophilic composition at a concentration of about 500 ppm, based on the total volume of the stabilized surfactant micelles 28.

The first dispersing apparatus 20 initiates and promotes formation of the micellar structures that are based on the bioactive component 12, the first aqueous composition 14 and the surfactant composition 16. Adsorption of surfactant component onto the surface of the bioactive component 12, or hydrophilic composition continues until all of the surfactant molecules cover, and therefore, entrap the bioactive component 12 or hydrophilic composition in the core of the micellar structure to form surfactant micelles 22. Formation of a plurality of surfactant micelles 22 in the first aqueous composition 14 forms a dispersion of surfactant micelles 22.

In general, any conventional dispersing apparatus 20 that is capable of homogenously blending or dispersing may be suitable for use in forming the dispersion of surfactant micelles in accordance with the present invention. Furthermore, those of ordinary skill in the art will recognize that the first dispersing apparatus 20 may vary depending upon the desired characteristics of the nanocapsules 36. For example, the first dispersing apparatus 20 may include any device, such as a sonicating or a vortexing apparatus (not shown), or the like to disperse the bioactive component 12 in the hydrophilic composition, and the formation of the surfactant micelles 22 after addition of the surfactant composition 16. Nonetheless, while the first dispersing apparatus 20 may include a sonicating or a vortexing apparatus, the sonicating or the vortexing apparatus is not critical when practicing the method of the present invention.

As used herein, a "surfactant micelle" may be characterized as a close packed mono-molecular barrier of surfactant molecules at an interface between the bioactive composition 12 and the surfactant composition 16, such that the barrier encapsulates the bioactive component 12, the first aqueous composition 14 or the hydrophilic composition. It is also to be understood that the term "surfactant micelle" encompasses partial or hemi-surfactant micelles that partially enclose the bioactive component 12, the first aqueous composition 14 or the hydrophilic composition.

When the bioactive component 12 is a hydrophilic bioactive component, the polar portion of the surfactant molecule associates with a surface of the hydrophilic bioactive component. When the bioactive component 12 is a hydrophobic bioactive component, the hydrocarbon portion of the surfactant micelle associates with a surface of the hydrophobic bioactive component.

The formation of a surfactant micelle typically occurs at a well defined concentration known as the critical micelle concentration. As noted, surfactant components having a CMC value of less than about 200 micromolars are preferred when practicing the present invention.

After forming the dispersion of surfactant micelles 22, the dispersion of surfactant micelles 22 is transferred into the stabilizing apparatus 26 where a biocompatible polymer component 24 is added to stabilize the dispersion of surfactant micelles 22. Alternatively, the biocompatible polymer component 24 may be added to the dispersion of surfactant micelles 22 in the first dispersing apparatus 20 which obviates the need for the stabilizing apparatus 26.

The biocompatible polymer component 24 stabilizes the dispersion of surfactant micelles 22 to form stabilized surfactant micelles 28 within the first aqueous composition 14. Therefore, a dispersion of stabilized surfactant micelles 28 are present within the first aqueous composition 14 after addition of the biocompatible polymer component 24.

As used herein, the term "biocompatible" refers to a material that is capable of interacting with a biological system without causing cytotoxicity, undesired protein or nucleic acid modification or activation of an undesired immune response.

The biocompatible polymer component 24 may be introduced into the dispersion of surfactant micelles 22 as a liquid, vapor or in granular form. The form of the biocompatible polymer component 24 that is selected preferably permits the biocompatible polymer component 24 to (1) remain stable prior to addition into the dispersion of surfactant micelles 22, (2) be homogeneously dispersed into the dispersion of surfactant micelles 22, (3) increase a viscosity of the first aqueous composition 14, (4) form a boundary layer at an interface of the surfactant micelle 22 and the first aqueous composition 14, (5) be absorbed onto a surface of the surfactant micelles 22, (6) be capable of iontophoretic exchange, (7) be capable of being precipitated upon addition of a solute, (8) be capable of enzymatic degradation, surface and/or bulk erosion, (9) not interfere with or mask the functional activity of the bioactive component 12, (10) prevent aggregation and/or agglomeration of the dispersion of surfactant micelles 22, and (11) be capable of obtaining a particular dissolution profile.

The biocompatible polymer component 24 may be included at an amount that is effective to coat and therefore stabilize the surfactant micelle 22. Furthermore, those of ordinary skill in the art will recognize that the amount of the biocompatible polymer component 24 used to stabilize the surfactant micelles 22 may vary depending upon the bioactive component 12, the first aqueous composition 14, the surfactant composition 16, the temperature, pH, osmolarity, presence of any optional solutes or optional solvents, the surfactant micelle 22, any desired characteristics of the stabilized surfactant micelle 28, the nanocapsules 36, or a desired dissolution profile.

While the concentration of the biocompatible polymer component 24 is not critical to the present invention, the concentration of the biocompatible polymer 24 is preferably based upon the bioactive component 12 and on the desired dissolution profile. When the concentration of the biocompatible polymer component 24 is too high, the shell of the nanocapsule 36 may not dissolve. If the concentration of the biocompatible polymer component 24 is too low, the shell of the nanocapsule 36 may dissolve rapidly in a manner that promotes cytotoxicity, for example. In addition, too low a concentration of the biocompatible polymer component 24 may not provide an effective degree of mechanical force to stabilize the surfactant micelles 28.

Concentrations of the biocompatible polymer component 24 that are too high may also be less desirable because such higher concentrations may increase the viscosity of the first aqueous composition 14, and consequently may cause difficulties in preparing, mixing and/or transferring the stabilizer surfactant micelles 28. Concentrations of the biocompatible polymer component 24 that are too low may be less preferred, because lower concentrations may not provide the needed viscosity to stabilize the surfactant micelles 22, nor be capable of effectively coating the surfactant micelles 22 to prevent aggregation of the surfactant micelles 22 in the first aqueous composition 14.

The biocompatible polymer component 24 may be supplied as individual biocompatible polymers or supplied in various prepared mixtures of two or more biocompatible polymers that are subsequently combined to form the biocompatible polymer component 18. Some non-exhaustive examples of biocompatible polymers include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methylmethacryl ate), poly(ethylmethacrylate), poly(butylmethacrylate), poly(isobutylmethacrylate), poly(hexlmethacrylate), poly(isodecylmethacrylate), poly(laurylmethacrylate), poly(phenylmethacrylate), poly(methacrylate), poly(isopropacrylate), poly(isobutacrylate), poly(octadecacrylate), polyethylene, polypropylene poly(ethylene glycol), poly(ethylene oxide), poly(ethylene terephthalate), poly(vinyl alcohols), poly(vinyl acetate), poly vinyl chloride, polystyrene, polyhyaluronic acids, casein, gelatin, gluten, polyanhydrides, polyacrylic acid, alginate, chitosan, any copolymers thereof, and any combination of any of these.

Additionally, biocompatible polymers that have been modified for desirable enzymatic degradation, or change upon application of light, ultrasonic energy, radiation, a change in temperature, pH, osmolarity, solute or solvent concentration may also be included as part of the biocompatible polymer component 24. Preferably, the biocompatible polymer component 24 is a hydrophilic polymer that is capable of substantially coating, and preferably continuously coating the surfactant micelle 22. Still more preferably, the hydrophilic biocompatible polymer component 24 is capable of ionotophoretic exchange.

Though descriptions of the present invention are primarily made in terms of a hydrophilic biocompatible polymer component 24, it is to be understood that anyotherbiocompatible polymer, such as hydrophobic biocompatible polymers may be substituted in place of the hydrophilic biocompatible polymer, in accordance with the present invention, while still realizing benefits of the present invention. Likewise, it is to be understood that any combination of any biocompatible polymer may be included in accordance with the present invention, while still realizing benefits of the present invention.

In general, any conventional apparatus and technique that is suitable for permitting the biocompatible polymer component 24 to stabilize the surfactant micelles 22 may be used as the stabilizing apparatus 26 in accordance with the present invention. Furthermore, any other device, such as high pressure homogenization or high ultrasound sonication is preferably not included during stabilization.

After stabilizing the surfactant micelles 22, the stabilized surfactant micelles 28 may be transferred into a second aqueous composition 30 located in a second dispersing apparatus 32. The stabilized surfactant micelles 28 may be transferred by mechanically forming droplets of the stabilized surfactant micelle 28 that are subsequently introduced into the second aqueous composition 30.

The second aqueous composition 30 may include water only, or may optionally include a solute to precipitate the biocompatible polymer component 24 surrounding the stabilized surfactant micelle 28. Some non-exhaustive examples of solutes that may be used to precipitate the biocompatible polymer 24 include ionic species derived from elements listed in the periodic table.

Preferably, the second aqueous composition 30 includes a solute in an amount that is effective to precipitate the biocompatible polymer component 24 and form the dispersed, and optionally atomized nanocapsules 36 of the present invention. As used herein, the term "precipitate" refers to a solidifying or a hardening of the biocompatible polymer component 24 that surrounds the stabilized surfactant micelles 28. It is also to be understood that the term "precipitation" is also meant to encompass any crystallization of the biocompatible polymer 24 that may occur when the biocompatible polymer component 24 is exposed to the solute.

Additionally, any other component that is capable of modulating the efficacy the nanocapsules 36 may be included as part of the second aqueous composition to thereby modulate the functional activity of the nanocapsule 36. For example, the second aqueous composition may include additional coating excipients, such as a cell recognition component or various ionic species, such as $Mn^{2+}$, $Mg^{2+}$, $Ca^{2+}$, $Al^{3+}$, $Be^{2+}$, $Li^+$, $Ba^{2+}$, $Gd^{3+}$, or any other ionic species that is capable of interacting with the biocompatible polymer component 24.

The term "cell recognition component", as used herein, refers to a molecule capable of recognizing a component on a surface of a targeted cell. Cell recognition components may include an antibody to a cell surface antigen, a ligand for a cell surface receptor, such as cell surface receptors involved in receptor-mediated endocytosis, peptide hormones, and the like.

It has been observed that when the stabilized surfactant micelles 28 are allowed to incubate in the second aqueous composition 30 that includes the solute to precipitate the biocompatible polymer component 24, the nanocapsules 36 undergo a reduction in size. Furthermore, the formation of a flocculated suspension of the nanocapsules 36 has also been observed after incubating the stabilized surfactant micelles 28 in the second aqueous composition.

As used herein, "a flocculated suspension" refers to the formation of a loose aggregation of discrete particles held together in a network-like structure either by physical absorption of bioactive components, bridging during chemical interaction (precipitation), or when longer range van der Waals forces of attraction exceed shorter range forces of repulsion. The flocculated suspension of nanocapsules 36 may entrap varying amounts of the first aqueous composition 14 or the second aqueous composition 30 within the network-like structure. Additionally, the flocculated suspension of nanocapsules may be gently tapped to disperse the nanocapsules 36.

The stabilized surfactant micelles 28 may be transferred into the second aqueous composition 30 via atomization through a nozzle (not shown) having a particular orifice size or through an aerosolizing apparatus (not shown). Atomizing or aerosolizing the stabilized surfactant micelles 28 typically includes the application of a shear force that may be capable of further dispersing the stabilized surfactant micelles 28. Furthermore, the application of the shear force during transfer may also be effective to (1) reduce the size of the nanocapsules 36, or (2) break up any agglomerates or associations between stabilized surfactant micelles 28 that may have formed in the stabilizing apparatus 26. Feed pressures of less than about 100 psi to the nozzle, for example, may be used to atomize the stabilized surfactant micelles 28.

The diameter of the nanocapsules 36 may also be varied depending upon the orifice size of the nozzle that may be used to transfer the stabilized surfactant micelles 28 into the second aqueous composition. Alternatively, the stabilized surfactant micelles 28 may be added to the second aqueous composition 30 containing the solute that precipitates the biocompatible polymer 24 to form a dispersion of nanocapsules 36 for purposes of providing the dispersion for subcutaneous delivery of the nanocapsules, for example.

After precipitating and/or optionally incubating the nanocapsules 36 in the second aqueous composition 30, the nanocapsules 36 may be filtered, centrifuged or dried to obtain separate and discrete nanocapsules 36. The nanocapsules 36 may be frozen or reconstituted for later use or may be delivered to a target cell or tissue by such routes of administration as oral, intravenous, subcutaneous, intraperitoneal, intrathecal, intramuscular, inhalational, topical, transdermal, suppository (rectal), pessary (vaginal), intra urethral, intraportal, intrahepatic, intra-arterial, intraocular, transtympanic, intraumoral, intrathecal, transmucosal, buccal, or any combination of any of these.

The nanocapsules 36 having a diameter of less than about 50 nm are advantageous in the delivery of bioactive components to target cells for several reasons. First, nanocapsules 36 having a diameter of less than about 50 nm enhances delivery of bioactive components by protecting the bioactive components against degradation during transport to the target cell.

Second, nanocapsules 36 having a diameter of less than about 50 nm promotes efficient cellular uptake. Efficient cellular uptake into the target cell typically occurs when a particle has a diameter of less than about 50 nm, as opposed to when a particle has a diameter of more than about 50 nm.

Third, it is believed that uptake of the nanocapsules 36 by the target cell occurs via transport systems, such as a non-endosomal pathway, that prevents lysosomal degradation of the nanocapsules 36. Indeed, it is believed that the nanocapsules 36 of the present invention are efficiently exported into a cell via a caveolin-regulated pathway that circumvents most, if not all, endosomal-regulated pathways that typically degrade nanocapsules 36.

Fourth, the nanocapsules 36 have a biocompatible polymer shell that is separate from the bioactive component. In fact, the bioactive component is not entangled in, embedded in, or adsorbed onto the biocompatible polymer shell of the nanocapsules 36. When the bioactive component is not entangled in, embedded in, or adsorbed onto the biocompatible polymer shell, the cell that incorporate the nanocapsules 36 avoid apoptosis or cell death.

Fifth, enclosing the bioactive component within a core surrounded by the biocompatible polymer shell when preparing the nanocapsules 36 in accordance with the present method is advantageous in avoiding premature degradation of the nanocapsules 36, or a cytotoxic response during in vivo transport of the nanocapsule. Enclosing the bioactive component within the core results in a linear release rate of the bioactive component without any zero burst phenomenon during release from the nanocapsules 36.

The linear release rate of the bioactive component from the nanocapsule without any zero burst phenomenon is also an advantageous feature as the linear release rate allows rational design of coating dissolution profiles to minimize cytotoxicity. As used herein, the term "dissolution profile" refers to a rate at which the biocompatible polymer shell is dissolved or degraded to release a bioactive agent from a core of a nanocapsule.

Another benefit of the nanocapsules 36 prepared by the method of the present invention is that little, if any, addition of an organic solvent is required to form the nanocapsules 36. Eliminating the use of most, if not all, organic solvents from the method of the present invention is beneficial since organic solvents may damage the bioactive component 12, destroy the target cells, or be toxic during preparation of the nanocapsule 36. The elimination of most, if not all, use of organic solvents eliminates the need for complex solvent removal techniques, such as solvent dilution, vacuum evaporation, or the like, and obviates any associated costs or complex process strategies during preparation of the nanocapsules 36.

The nanocapsules 36 of the present invention further permits stable encapsulation of a bioactive component, and in particular, hydrophilic bioactive components, such as polynucleotides and polypeptides. "Stable encapsulation", as used herein, refers to maintenance of the encapsulated bioactive component's structure. For nucleic acids, the appearance of low molecular weight nucleic acid breakdown products, which maybe assayed for by electrophoresis, is substantially eliminated. The nanocapsules 36 may also be used to encapsulate any bioactive component regardless of water solubility or charge density.

APPLICATIONS

The nanocapsules 36 may be combined with additional polymeric binders, surfactants, fillers, and other excipients to incorporate the nanocapsules 36 into solid dosage forms such as granules, tablets, pellets, films or coatings for use in enhanced bioactive component 12 delivery. In this way, design of the dissolution profile, control of the particle size, and cellular uptake remains at the level of the nanocapsule. Such applications include, but are not limited to, creation of rapidly dissolving pellets of nanocapsules for pulmonary delivery or nanocapsule films for device-mediated delivery.

In another application, the nanocapsules 36 may be designed for specific cellular or tissue uptake by polymer selection and/or inclusion of cell-recognition components in the nanocapsule biocompatible polymer shell or coating. Such coatings will have utility for specific or increased delivery of the bioactive agent to the target cell. Such applications include, but are not limited to tumor-targeting of chemotherapeutic agents or anti-sense DNA, antigen delivery to antigen-presenting cells, ocular delivery of ribozymes to retinal cells, transdermal delivery of protein antibodies, or transtympanic membrane delivery of peptide nucleic acids.

Property Determination and Characterization Techniques

Figure 2A:
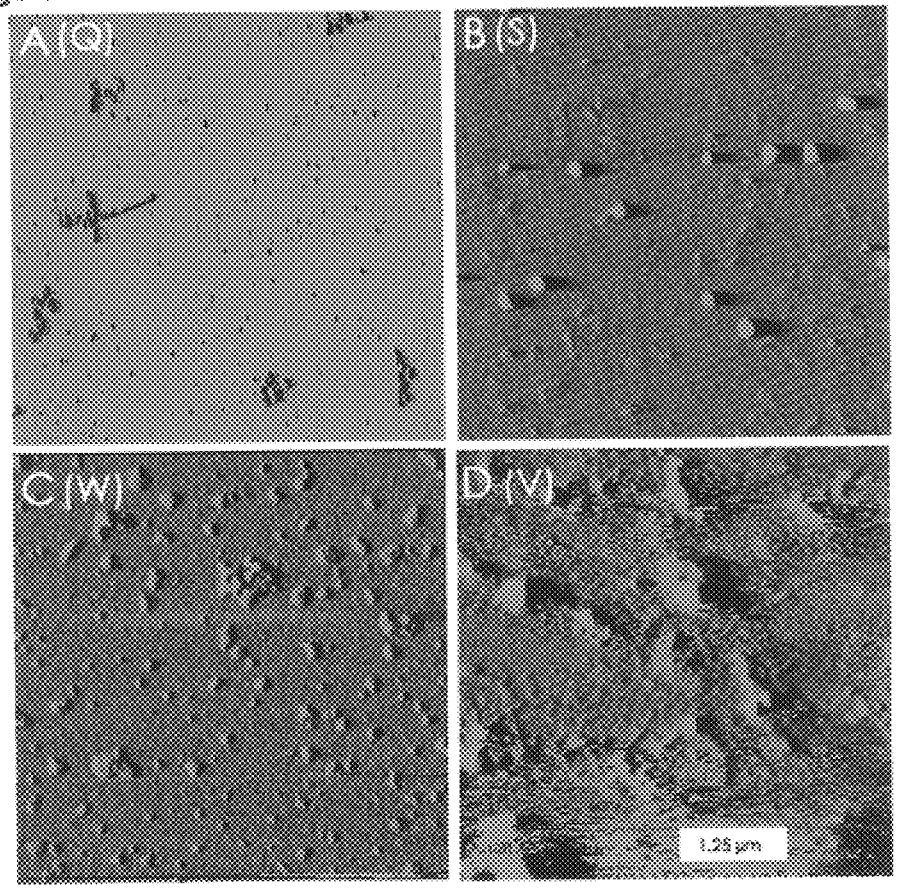
FIG. 2A: "Nanocapsules prepared under different dispersion conditions" illustrates atomic force microscopy of nanocapsule formulations prepared under different dispersion conditions.

Various analytical techniques are employed herein. An explanation of these techniques follows:

FIG. 2A: Samples were prepared on freshly cleaved mica as dispensed, dried in air and imaged using a Nanoscope II multimode AFM (Digital Instruments) with a J type scanner and ambient tapping mode holder. 125 μm long silicon cantilevers type IBMSC were from IBM and have resonant frequencies of 250–450 kHz. Due to the size similarity of the AFM cantilever tip to the size capsules, reported particle diameter may vary by as much as 50%. All imaging was in tapping mode, images were 512×512 pixels and scanning frequency was 1 kHz. Height, amplitude and phase images were collected. Images were processed in DI software and analyzed in NIH Image SXM. A: Formula Q from 2-phase system, low HLB surfactant, B: Formula S from 2-phase system, high HLB surfactant, C: Formula T from 1-phase system, high HLB surfactant, D: Formula V from 2-phase system, surfactant below CMC.

Figure 2B:
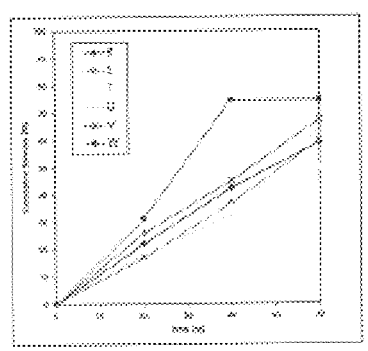
FIG. 2B: "Cumulative release studies for nanocapsule formulations" illustrates results from an experiment documenting quantitative recovery of small amounts of DNA from releasing solutions.

FIG. 2B: Nanocapsules were released into a solution of 10% isobutanol in Phosphate-buffered Saline (PBS), pH=7.2. Samples were run in duplicate.

Figure 2C:
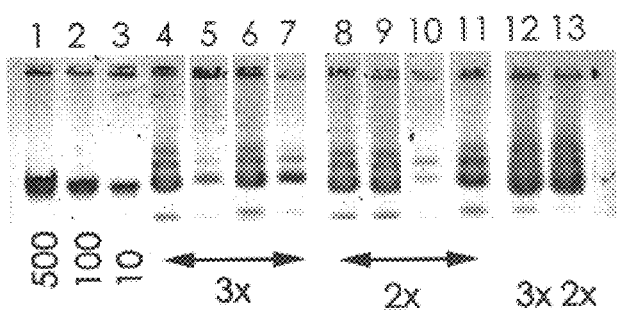
FIG. 2C: "Quantitative recovery of DNA from receiver solutions" illustrates cumulative release over 72 hours for nanocapsules prepared under different dispersion conditions.

FIG. 2C: Nominal 300 ng samples of DNA were aliquoted from a master batch containing surfactant and processed through commercial miniprep columns. Eluate was recycled through Qiaquik™ columns and collected either 3 times (4, 5) or twice (6, 7) or recycled through Zymoclean™ columns and collected twice (8, 9). Samples were alcohol precipitated using a commercial coprecipitant, electrophoresed on 1.5% agarose gels modified with Synergel™, stained with SybrGold™ dye, digitized on a Storm 860™ and compared to unmodified but reprecipitated samples from the same master batch (10, 11). Lanes 1–3: 100, 50 and 5 ng of lambda-DNA.

Figure 3:
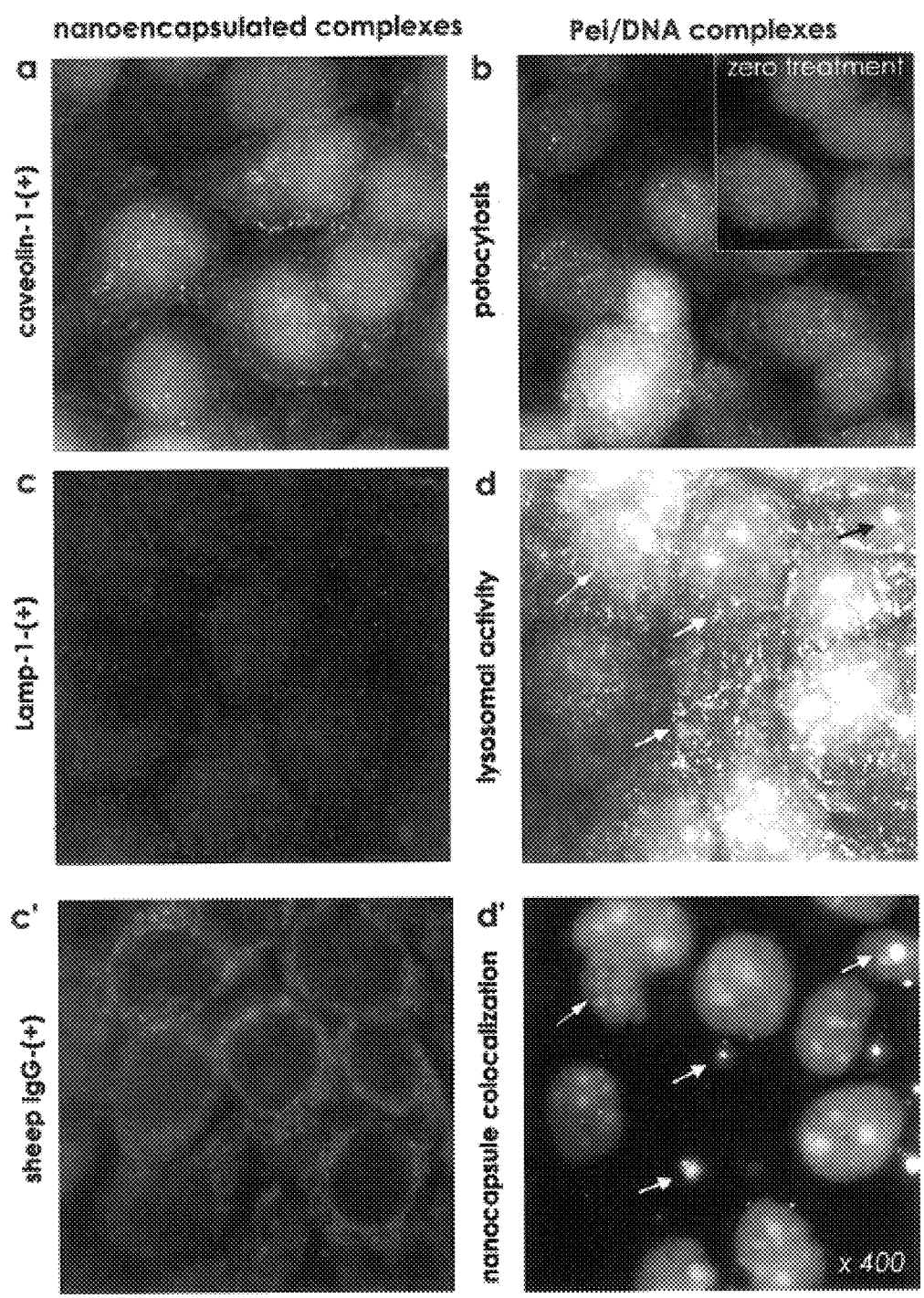
FIG. 3: "Nanocapsule modulation of cellular uptake" illustrates relative pinocytotic activity of HacaT keratinocyte cultures treated with DNA complexes, nanocapsules containing DNA or no treatment.

FIG. 3: Endocytic activity was assessed by immunosignal levels of clathrin (Chemicon). Potocytotic activity was assessed by immunosignal for caveolin-1 as described in the literature (Transduction Laboratories). Lysosomal activity was detected by a monoclonal antibody to Lamp-1 (Transduction Laboratories). Nanocapsule coatings were spiked with ovine IgG to enable this detection strategy.

Figure 4:
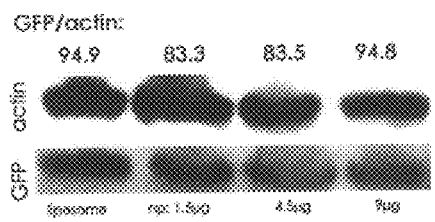
FIG. 4: "Dose response for a nanocapsule formula" illustrates western blotting of total protein from rat fibroblast cultures.

FIG. 4: Immortalized Rt-1 fibroblast cultures at 70% confluence were treated for 4 days with increasing amounts of nanocapsule formula K and transiently treated (3 hours) with an optimized liposomal formula (dosed, 500 ng) Results are expressed as a percentages of cellular actin integrated intensity and compared to the liposomal formula. Expression vector was code 448: pEF/myc-his/GFP (Invitrogen).

Figure 5A:
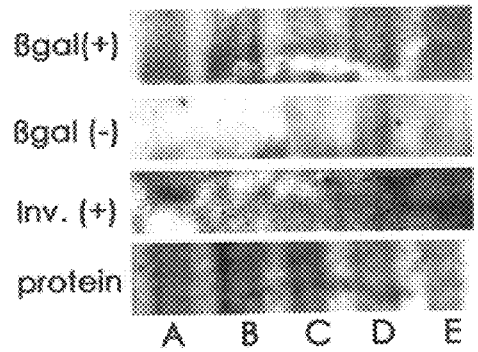
FIG. 5A: "Nanocapsule-delivered transgene production in porcine dermis" illustrates western blotting of porcine dermal tissue.

FIG. 5A: Radiated porcine biopsies were snapfrozen 7 days after treatment with saline or 6 μg of controlled release nanocapsules, then homogenized in RIPA. 100 μg lysate samples were electrophoresed on SDS-Page gradient gels, transferred to nitrocellulose membranes and detected for either beta-galactosidase (about 121 kilo Dalton (kD)) or involucrin (about 100 kD) using chemiluminescence. Results were normalized to the post-transfer gel stained with Coomassie due to interference at 100 kD from a gel defect. Involucrin, a component of the cornified membrane, manufactured by suprabasal cells can be detected in radiated porcine skin and used for future normalization purposes. Lane A: N, topical, biopsy oc-2; B: N, topical, biopsy oc-3; C: O, topical, biopsy 1—1; D: PBS only, biopsy 1–5; E: N, subcutaneous injection, biopsy 1–6.

Figure 5B:
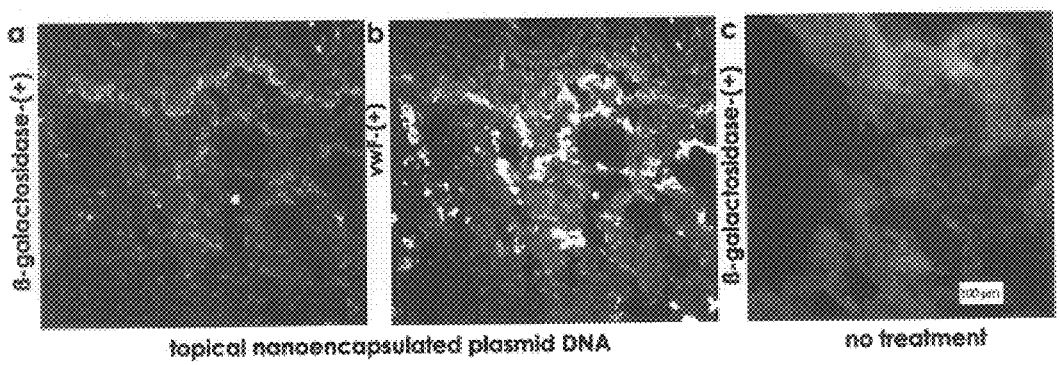
FIG. 5B: "Macromolecule delivery across keratinized barrier epithelial" illustrates immunofluorescence microscopy of porcine dermal tissue sections from organ culture study demonstrating topical nanocapsule delivery across keratinized barrier epithelial.

FIG. 5B: The beta-galactosidase reporter protein was detected by a monoclonal antibody directed at an incorporated fusion protein tag. A: N, topical, biopsy oc-1, detection with anti-Xpress™; B: Matching view to A with detection for anti-von Willenbrand factor (Sigma); C: untreated biopsy, detection with anti-Xpress™ (Invitrogen).

Figure 6:
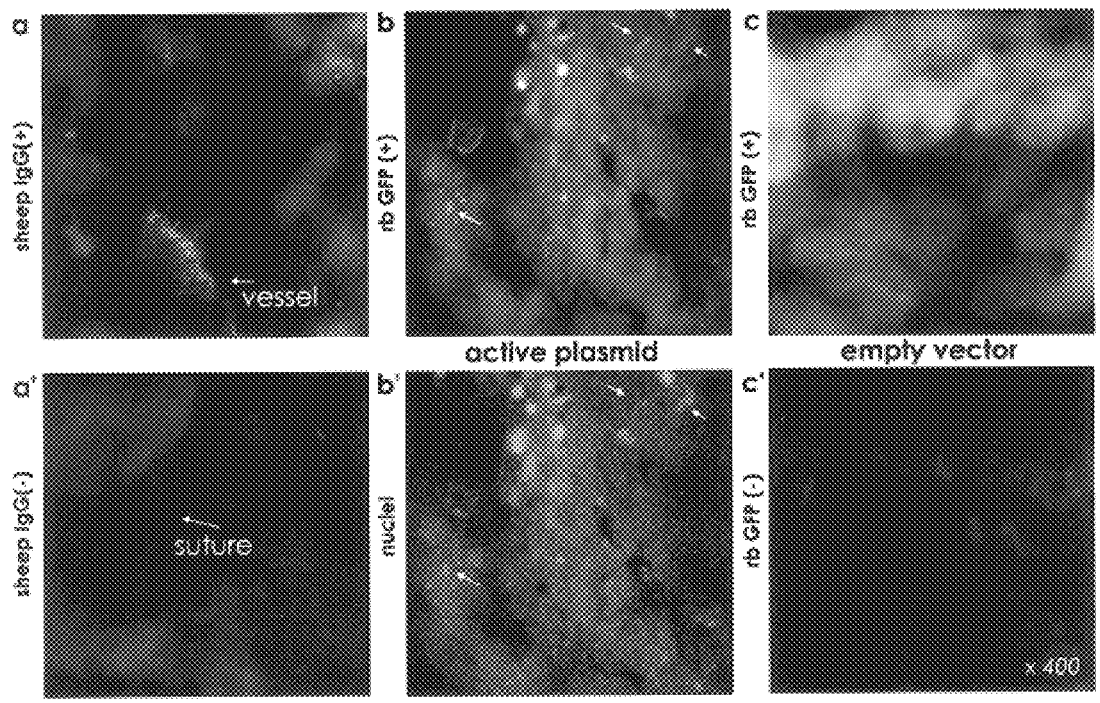
FIG. 6: "Incorporation of nanocapsules into a suture" shows incorporation of nanocapsules into a solid dosage form.

FIG. 6: Nanocapsules were incorporated into an aqueous suture coating and sutures were applied to pigskin biopsies in organ culture. Nanocapsules were detected with Cy3 conjugated-streptavidin-biotin complexes to incorporated ovine IgG and nuclear localized GFP transgene expression was detected by rabbit polyclonal antibodies to GFP (Abcom) in combination with Fitc-conjugated polyclonal antibodies to rabbit IgG and Alexa 488-conjugated polyclonal antibodies to Fitc (Molecular Probes). Cell nuclei were counterstained with 10 µg/ml bisbenzamide. Controls omitting primary antibodies were included for specificity determination and signal-to-background level estimation.

Figure 7A:
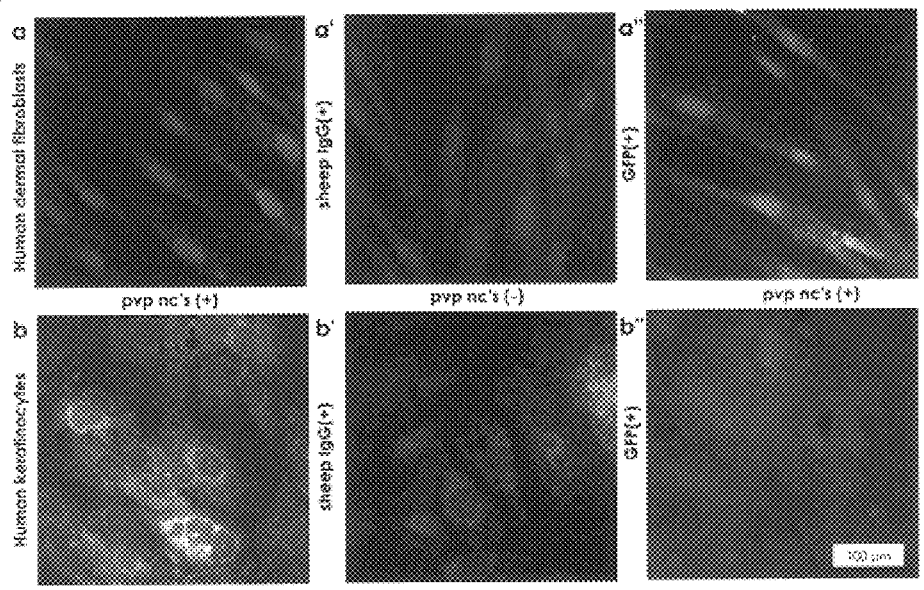
FIG. 7A: "PVP nanocapsules are taken up by fibroblasts but not keratinocytes" illustrates polyvinylpyrrolidone nanocapsule uptake and Green Fluorescent Protein (GFP) expression in 35 mm human dermal fibroblast and immortalized keratinocyte cultures.

FIG. 7A: Nanocapsules were detected as previously described and nuclear-localized GFP transgene expression was detected by rabbit polyclonal antibodies to GFP in combination with Cy3-conjugated antibodies to rabbit IgG (Jackson Laboratories).

Figure 7B:
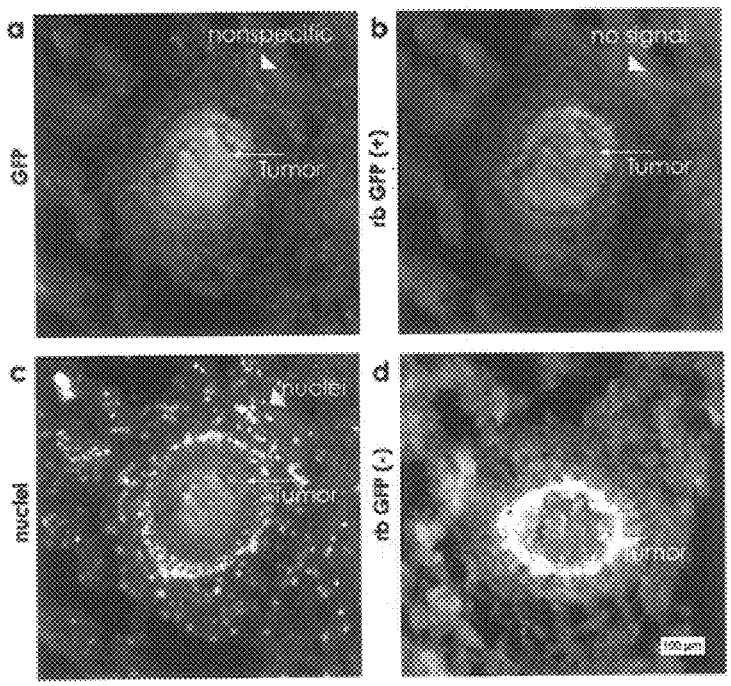
FIG. 7B: "Nanocapsule design for tumor-targeting" illustrates tumor targeting of GFP plasmid DNA by Tenascin nanocapsules.

FIG. 7B: GFP expression was detected as described in FIG. 6 and cell nuclei were counterstained with 10 µg/ml bisbenzamide.

Figure 7C:
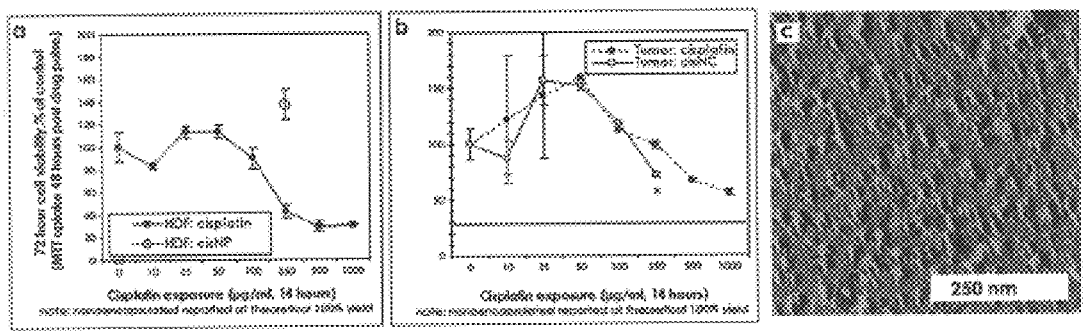
FIG. 7C: "Nanocapsule coating design for increased drug safety" illustrates an effect of nanocapsules that are coated with Tenascin and nanocapsules that are not coated with Tenascin on growth inhibition of squamous cell carcinoma and human dermal fibroblast (HDF) cultures.

FIG. 7C: Carcinoma cells and HDF's were seeded overnight into 96 well plates at 2000 and 6000 cells per well respectively. Cisplatin preparations were added to wells for 18 hours as noted on the graph than washed out. After 72 hours, cell viability was assessed by a commercial MTT assay (WST assay, Boehringer Mannheim). Wells were executed in duplicate.

Figure 8A:
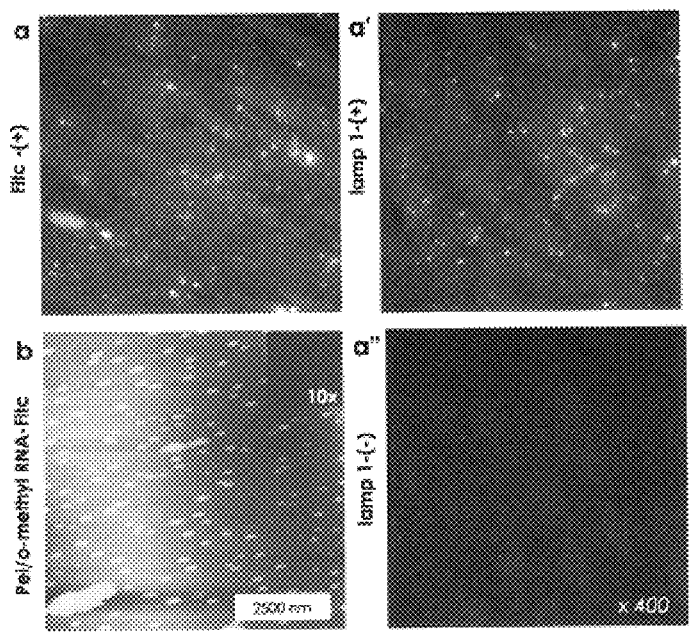
FIG. 8A: "Cellular uptake and lysosomal sequestration of RNA oligomers complexed with polyethyleneimine" shows uptake of HDF cultures treated with nanocapsules containing 20 mer Fitc-labeled O-methyl RNA oligonucleotides.
Figure 8B:
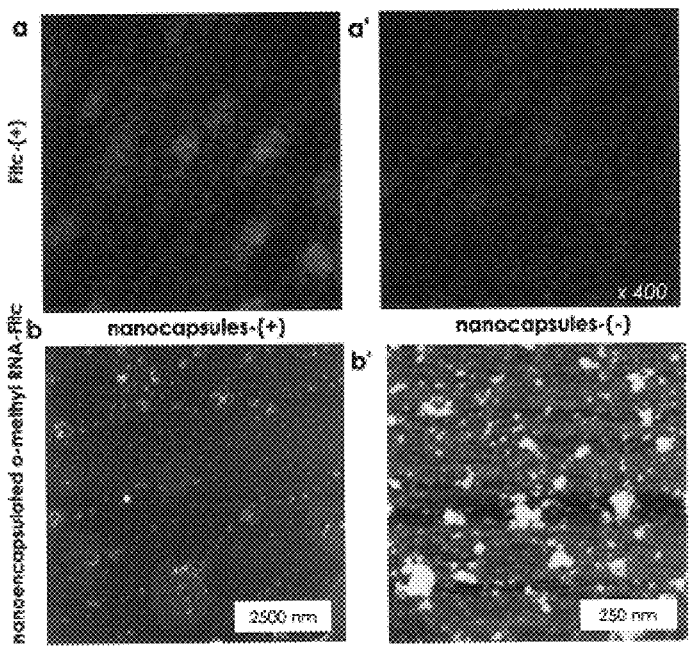
FIG. 8B: "Nanocapsules avoid lysosomal sequestration at 18 hours post-addition" shows uptake of HDF cultures treated with nanocapsules containing 20 mer Fitc-labeled O-methyl RNA oligonucleotides.

FIGS. 8A and 8B: Colocalization with lysosomes was detected using a monoclonal antibody to Lamp-1 (Transduction Laboratories). AFM images are included of O-methyl RNA formulated by nanoencapsulation or complexation with 27 kD polyethyleneimine.

EXAMPLES

The present invention is more particularly described in the following Examples which are intended as illustrations only since numerous modifications and variations within the scope of the present invention will be apparent to those skilled in the art.

Reagents
A. Nucleic Acid Condensing Agents

Poly(ethylenimine) (PEI) at 27 KiloDalton (kD). PEI was used at optimized conditions (90% charge neutralization)

Polylysine (PLL) at 70–150,000 molecular weight. PLL condensing materials were conjugated with nuclear signal localization peptides, either SV-40 T antigen or cys-gly-tyr-gly-pro-lys-lys-lys-arg-lys-val-gly-gly using carboxiimide chemistry available from Pierce Chemical (Rockford, Ill.).

Preparations of nuclear matrix proteins (NMP). NMP were collected from a rat fibroblast cell line, and a human keratinocyte cell line using a procedure described in Gerner et al. *J. Cell. Biochem.* 71 (1998):363–374 which is incorporated herein by reference. Protein preparations were conjugated with nuclear signal localization peptides as described.

B. Surfactants 2,4,7,9-tetramethyl-5-decyn-4,7-diol (TM-diol): HLB= 4–5, CMC is not determined Poly(oxy-1,2-ethanediol), a-(4-nonylphenol)-w-hydroxy, Tergitol NP-40 (NP40), Nonoxynol-40, POE (40) nonyl phenyl ether: HLB=17.8, CMC 232 µM, Polyoxyethylene 80 sorbitan monooleate (Tween 80): HLB=10, CMC 12 µM, Cetyl Alcohol: HLB=4, CMC is not determined.

C. Polymers

Hyaluronan, recombinant, 1 million kiloDalton (MM kD) and conjugated with nuclear localization signal peptides as described in U.S. Pat. No. 5,846,561, which is incorporated herein by reference.

Hyaluronan, derived from human umbilical cord, about 4 MM kD and not conjugated.

Povidone (polyvinylpyrrolidone, PVP) 10,000 kD MW and not bioconjugated.

Povidone (polyvinylpyrrolidone, PVP) 40,000 kD MW and not bioconjugated.

Povidone (polyvinylpyrrolidone, PVP) 360,000 kD MW and not bioconjugated.

Tenascin, 220 kD and not bioconjugated.

D. Expression Vectors

334: pcDNA/His/LacZ, produces beta-galactosidase, incorporates CMV promoter, based on pcDNA 3.1. (Invitrogen), 8.6 kilobases 425: pEGFP-c/farn, enhanced GFP (green fluorescent protein) expression vector modified with a famasyl moiety to improve microscopy, CMV promoter, 4.6 kB 423: pEGFP-c3/p57(Kpn/Sma) Clontech enhanced GFP (green fluorescent protein) expression vector modified with a nuclear localization tag from a cyclin dependent kinase to improve microscopy, 4.6 kB E. Cells CCRL 1764: Immortalized rat neonatal fibroblast cell line (RT-1's)

HaCaT: immortalized human keratinocyte cell line

Ca9: human tumor cells derived from a squamous cell carcinoma of tongue origin.

Example 1A

Effect of Changing Dispersion Conditions on Hydrophillic Nanocapsules

The importance of appropriate dispersion conditions was investigated in the following series of formulations. Formulae were produced by i) predispersing 25 µg of DNA (425) on ice using a bath sonicator, ii) condensing DNA in a small amount of water by vortexing then incubating on ice for 20 minutes, iii) adding surfactant then oil followed by 30 seconds of probe sonication at 10 Watts, iv) dispersion dilution to 3 milliliters (mL) by first adding saline then 1 MM kD hyaluronan polymer (1%) as a protective colloid with bath sonication, v) mechanically shearing emulsion into droplets by pumping through a 250 micrometer (µm) orifice into 22 mL of PBS, 10 millimolar (mM) $Ca^{2+}$, 200 mM $Li^+$, vi) incubating overnight end over end and vii) centrifuging to recover nanoparticles for resuspension and filter sterilization. The condenser-to-DNA weight ratio was determined by dye exclusion at 90% charge neutralization. TM-diols were used in this experiment to represent water-immiscible surfactants, while Tergitol NP40 and Tween 80 were used to represent water-soluble and even more water-soluble emulsifiers/dispersing aids.

Dispersion conditions were systematically varied to discourage micelle formation in aqueous media by i) choosing water-soluble surfactants (Formulae S,T,U, W and V), ii) removing the dispersed phase (Formula T) and iii) decreasing surfactant loading below that required for micelle formation (Formula V). Formula U featured use of a water-immiscible oil (silicone oil). Formulas were characterized physically and tested for functionality in in vitro gene transfer. Quantitative results are summarized in Table 1A:

TABLE 1A

Effect of changing dispersion conditions on hydrophillic nanocapsules.

| Formula | Q | R | S |
|---|---|---|---|
| Experimental Modification: | | | |
| Critical Micelle Concentration | surf > CMC | surf > CMC | surf > CMC |
| (CMC) | ~0 | ~0 | 460 ppm |
| Pre-aerosol surfactant Concentration (3 ml basis) | 500 ppm | 500 ppm | 600 ppm |
| HLB number | 4–5 | 4 | 17.8 |
| Phases | Water/misc. oil | Water/misc. oil | Water/misc. oil |
| Formula Characteristics: | | | |
| Nucleic Acid Incorporation (%) | 86 ± 8 | 67 ± 1.4 | 50.3 ± 12 |
| Low MW DNA Appearance (% above background, Post nanocapsule digest by electrophoresis) | 15.00 | 76 | 93.00 |
| Supercoil retention (post 100 hrs release) (area %, initial distribution = 76% supercoiled) | 87% | 65% | 66% |
| Particle Size (mean ± SE) | 42 ± 2 | 45 ± 3 | 73 ± 4 |
| Secondary Structure(s) | 25% | 30% | 70% |
| Flocculation Status | 100–200 nm stringy flocs | 500 nm stringy flocs | 300 nm spheroid aggregates |
| Comments: | | | |
| Performance: | | | |
| Transduced GFP Protein Generation (pixel units, % of control liposome formula, 100 μg total protein, Day 11) | 420 | 340 | 0 |

| Formula | T | U | W | V |
|---|---|---|---|---|
| Experimental Modification: | | | | |
| Critical Micelle Concentration | surf > CMC | surf > CMC | surf > CMC | surf < CMC |
| (CMC) | 460 ppm | 460 ppm | 15 ppm | 460 ppm |
| Pre-aerosol surfactant Concentration (3 ml basis) | 600 ppm | 600 ppm | 4000 ppm | 90 ppm |
| HLB number | 17.8 | 17.8 | 10 | 17.8 |
| Phases | Water only | Water/ immisc. oil | Water/misc. oil | Water/misc. oil |
| Formula Characteristics: | | | | |
| Nucleic Acid Incorporation (%) | 39 ± 1.7 | 33 ± 6 | 37 ± 1.4 | 58 ± 16 |
| Low MW DNA Appearance (% above background, Post nanocapsule digest by electrophoresis) | 53.00 | 66 | 28 | 41.00 |
| Supercoil retention (post 100 hrs release) (area %, initial distribution = 76% supercoiled) | 59% | 43% | 65% | 80% |
| Particle Size (mean ± SE) | 226 ± 11 | 291 ± 25 | 150 ± 7 | 199 ± 11 |
| Secondary Structure(s) | S < 10% | S < 10% | S > 40% | S > 80% |
| Flocculation Status | | | yeast-like aggregates | 400 nm aggregates |
| Comments: | ppt. during aerosolization | | ppt. during aerosolization | ppt. during aerosolization |
| Performance: | | | | |
| Transduced GFP Protein Generation (pixel units, % of control liposome formula, 100 μg total protein, Day 11) | 0 | 0 | 0 | 0 |

Nanocapsule sizing was determined by tapping mode AFM and images are illustrated in FIG. 2A. The data indicate average nanocapsule sizes less than 50 nm are achievable only with multi-phase systems in combination with low water solubility surfactants (Table 1A: Formulae Q,R vs. S,T,U,V, and W). Furthermore, only nanocapsules of less than 50 nm resulted in detectable transgene production in CRL-1764 rat fibroblast cells (Table 1A). Effective dispersion also corresponded with decreased aggregation and enhanced DNA stability (as indicated by decreased electrophoretic breakdown products). The starting DNA was partially relaxed (76% supercoiled by electrophoresis). Using this value as a basis, supercoil retention in DNA still encapsulated following 100 hours of release testing, was excellent in multi-phase systems.

Release profiles for hydrophillic dispersed atomized nanocapsules were linear, showed no zero burst and resulted in about 60% release after 72 hours (See FIG. 2B). Formula W, manufactured with a standard surfactant (Tween 80) at a reasonable loading value (0.4%) failed to completely release loaded DNA. FIG. 2C illustrates that small amounts of DNA (in this case 300 nanograms of DNA) can be recovered accurately in a procedure comprising butanol extraction of 10% butanol/saline releasing fluid followed by isolation on a miniprep column and measurement of absorbance at 260 nm excitation. Results obtained from UV spectroscopy are confirmed by electrophoresis of recovered DNA following alcohol coprecipitation with a commercial coprecipitant aid. Experiment 1A demonstrates the importance of a multi-phase system in creating coated particles from the micellar solution, defines surfactant requirements and validates method for measuring in vitro release profiles.

Example 1B

Effect of Process Parameters on Particle Functionality

To investigate the effect of modulating process parameters on nanocapsule functionality for DNA delivery, a series of formulas (designed to release in 3 days) were prepared. The transduction efficiency of these formulas for delivering a nuclear Green Fluorescent Protein (GFP) reporter transgene in rat fibroblast cultures was measured 5 days later. Charge neutralization of the DNA molecule, the surfactant/oil system, total surfactant phase volume, the inclusion of probe sonication, the absolute requirement for atomization and receiving bath osmolality were modulated. Results for this experiment are summarized in the Table 1B:

TABLE 1B

Effective of process parameters on particle functionality

| Nano capsule Design | Formula Name | charge neutral-ization by condensor | Surf-actant | Bio-compatible Oil | Oil Phase Volume (%, 4.5 ml basis) | Emulsify by soni-cation | Atomize Diameter ($\mu$m) | Receiving bath Osmo-lality (mOs) |
|---|---|---|---|---|---|---|---|---|
| 1 | q.co.2 | + | Cetyl OH | Castor oil/Etoh | 4 | + | 250 | 220 |
| 2 | q.co | — | Cetyl OH | Castor oil/Etoh | 4 | + | 250 | 220 |
| 3 | o.35 | + | TM-diol | DMSO | 4 | + | 1.4 | 220 |
| 4 | ea0.2 | + | TM-diol | DMSO | 4 | — | — | 220 |
| 5 | ea0.1 | — | TM-diol | DMSO | 4 | — | — | 220 |
| 6 | ed0.2 | + | TM-diol | DMSO | 0.05 | — | 250 | 220 |
| 7 | ed0a.12.di | + | TM-diol | DMSO | 0.05 | — | 250 | 0 |

| Nanocapsule Design | Formula name | Nanocapsule diameter (nm)* n = 20 | Encapsulation yield (%, mean ± SE) | Transduction Efficiency, (5 days, rat fibroblasts) |
|---|---|---|---|---|
| 1 | q.co.2 | 20 ± 3, rods | 48.6 ± 11 | 87 ± 7% |
| 2 | q.co | 12 ± 0.7, irregular | 48.6 ± 2 | 71 ± 28% |
| 3 | o.35 | 17 ± 1.2, spheres | 82.3 ± 7 (4) | 86 ± 2% |
| 4 | ea0.2 | 24 ± 2, s/r | 32 ± 10 | 72 ± 2% |
| 5 | ea0.1 | 36 ± 3, irregular | 57 ± 2 | 85 ± 1% |
| 6 | ed0.2 | 39 ± 3, r/e | 39 ± 5 | 96% |
| 7 | ed0a12.di | 39 ± 3, ellipse | 69 ± 2 | 100% |

*Nanocapsule diameter is reported as average of the minor and major particle axis using digital image analysis, while nanocapsule morphology is reported as irregular, rods (r), ellipse (e) or spheres (s). As the radius of curvature for the AFM silicon cantilever can be 10–30 nm, dilation effects can result in diameter overestimates by as much as 50%.

Aqueous dispersions of DNA condensates with poorly soluble surfactants in the inventive method produced average nanocapsule diameters under 50 nm. A number of successful operating regimes were feasible with varying effects on encapsulation yield. In a cetyl alcohol/castor oil system, under condensation resulted in an average particle diameter decrease from 20 to 12 nm (Table 1B: F1 vs. F2). The same decrease in condenser weight ratio induced an average particle size increase from 24 to 36 nm, while still maintaining nanocapsule functionality for transgene delivery, when using a TM-dio/IDMSO surfactant system for initial micelle formation (Table 1B: F4 vs. F5). This finding teaches surfactant selection impacts final average nanocapsule diameters.

The removal of moderate energy input (dropped probe sonication, atomization but kept bath sonication) during nanocapsule formation resulted in functional particles with decreased yield (Table 1B: F3 vs. F4). This finding indicates that optimal nanocapsule production is not dependent on any spontaneous micro-emulsification process. Cosolvent phase volume was reduced from 4 weight percent to 500 ppm without any negative effect on particle functionality (Table 1B: F4 vs. F6). This finding indicates that essentially solvent-free nanocapsules can be made by the inventive method. Finally, salt was removed from the atomization receiving bath without any negative effects on nanocapsule functionality (Table 1B: F6 vs. F7).

Example 2

Effect of Nanocapsule Sizing on a Nanocapsule Uptake in Human Keratinocytes

The effect of nanocapsule sizing on intracellular trafficking in immortalized HacaT human keratinocyte cultures (HacaT's) was investigated in this example. In this series of formulae, three micellar dispersion were sheared by syringes of different orifice diameter. The coating weight was also lowered from 1:1 DNA: Polymer (w/w) to 1:40 to shorten the dissolution profile from 5 to 3 days. In these experiments, nanocapsule formulae were compared to standard polyplexes of DNA and PEI, and lipoplexed plasmid DNA. Table 2 summarizes the experimental design and results:

TABLE 2

Effect of particle size on nanocapsule functionality for gene transfer

| Formula Name | Particle Size (mean, nm: morphology) | 4 hr. colocalization with caveolin-1* | 4 hr. colocalization with clathrin | 10 hr. colocalization with lysosomes | Transduction Efficiency, (5 days, human keratinocytes) |
|---|---|---|---|---|---|
| o.22 | 47 ± 3, rods | 0 | ++ | + | 16 ± 13 |
| o.27 | 21 ± 2, rods | + | ++ | ND | 81 ± 8 |
| o.35 | 17 ± 1.2, spheres | +++ | 0 | 0 | 78 ± 9 |
| pei-pDNA | 67 ± 4, spheres, irreg. | 0 | +++ | +++ | 40 ± 15 |
| Lipoplex pDNA | 48 ± 2 200 nm aggregates | + | + | +++ | 41 ± 27 |

*Key:
0 = no change from unstimulated condition,
+ greater than 25% increase,
++ greater than 50% increase,
+++ greater than 75% increase in number of cells stimulated.
ND = not determined.

It was observed that compared to the unstimulated state, nanocapsules increased cellular pinocytotic activity relative to standard formulations, and smaller nanocapsules shifted pinocytotic fly activity to caveolae from clathrin-coated pits (Table 2: Formula O vs. pei-DNA and lipoplex pDNA). It was further observed that nanocapsules avoided lysosome co-localization at 10 hours post-addition with smaller nanocapsules being particularly effective (see Table 2: Formula O vs. pei-DNA and lipoplex pDNA). These results are illustrated further in FIG. 3. This improvement is further emphasized by comparison with published uptake studies for HacaT keratinocytes. Compared to primary keratinocytes, uptake of naked DNA oligonucleotides (20 $\mu$M) was very poor in HacaT's and showed accumulation of oligonucleotides in punctate vesicles consistent with lysosomes at 2 hours. In contrast, using hydrophillic dispersed atomized nanocapsules of the inventive method, complete avoidance of lysosomes at 10 hours post-addition was demonstrated (FIG. 3). These results indicate that products of the inventive process will have increased and prolonged effectiveness.

Example 3

Effect of Nanocapsule Delivery on DNA and Reapent-induced Cytotoxicity

To test whether soluble exogenous DNA released from liposomes or dendrimers induces apoptosis, Rt-1's were treated with loaded/unloaded liposome complexes, dendrimer complexes, nanocapsule and 1 $\mu$g/ml etoposide, a DNA intercalating agent as a positive control. Cultures were treated with standard formulas for 3 hours then assayed for gene product expression 30 hours later. Cultures were treated with nanocapsules for 4 days to ensure full DNA release during the experiment. Controls included as a positive control for apoptotic cell death, 1 $\mu$g/ml etoposide, a DNA intercalating agent that was applied to cultures overnight before experiment termination. Other controls included standard PEI-DNA complexes, empty nanocapsules and nanocapsules containing empty vector plasmid DNA. Hydrophillic nanocapsules were produced for this experiment as described earlier using a 35-gage syringe.

One of the later steps in apoptosis is DNA fragmentation mediated by activation of endonucleases as part of the apoptotic program. Therefore, DNA fragmentation was assayed by end-labeling of fragments using an exogenous enzyme and a substituted nucleotide (TUNEL: tdt-mediated uridine nucleotide and labeling. Results are expressed as a Fragmentation Index, or the percent of cells in the total culture exhibiting BRDU end-labeled DNA. Cultures were run in duplicate. The experimental design and results are summarized in Table 3:

TABLE 3

Effect of nanocapsule coating weight on nonspecific reagent and plasmid DNA-associated cytoxicity.

| Formula | Y.35 | Lipoplex GP | Lipoplex L+ | Polyplex |
|---|---|---|---|---|
| Particle Design: | | | | |
| DNA Condensing Agent | 27 kD PEI | cationic lipid | cationic lipid | dendrimer |
| Coating Ratio (DNA/polymer) | 0.0025 | | | |
| Performance: | | | | |
| dose: (30 hrs for Std. Formulas, 100 hrs for nanocapsules) | 5 | 1 $\mu$g 500 ng 0 ng | 500 ng 250 ng 0 ng | 2 $\mu$g 1 $\mu$g 0 $\mu$g |
| Cytotoxicity: (Fragmentation Index, %) cytotoxicity controls: (1 $\mu$g etoposide (8 hr): 25 ± 10%) | 9 ± 8 | 27 ± 8 6 ± 3 4 ± 2.5 | 9.3 ± 0.2 12.8 ± 1.5 7.8 ± 0.1 | 6.63 ± 1.4 5.7 ± 1.8 3.1 ± 0.3 |

TABLE 3-continued

Effect of nanocapsule coating weight on
nonspecific reagent and plasmid DNA-associated cytotoxicity.

| Formula | Y.35 | Lipoplex GP | Lipoplex L+ | Polyplex |
|---|---|---|---|---|
| (Pei-DNA polyplexes (100 hr): 24 ± 7%) | | | | |
| (Empty vector nanocapsules: 1.25 ± 1.25%) | | | | |
| (Empty vector nanocapsules: 0.9 ± 0.7%) | | | | |
| Transduction Efficiency: (% cells) 120 hrs, dose as listed) | 24 ± 4 | 17 ± 2 | dead | dead |
| Formula Characteristics: | | | | |
| Nucleic: Acid Incorporation: (%) | 667 ± 0.2 | ND | ND | ND |
| Cumulative Release: (%, 48 hr) | ND | ND | ND | ND |
| Particle Size (mean ± SE, nm) | 57 ± 5 | 48 ± 2 | ND | 22.4 ± 2 |
| Agglomerates (as dispensed) | g.t. 50% 300 nm | 300 nm | | 25% 300 nm hard-fused |

TABLE 3B

Dose response of nanoencapsulated pDNA

| Formula | Dose (100 hr.) | GFP/Actin Production (density ratio, %) |
|---|---|---|
| K.35 | 9 μg | 94.8 |
| K.35 | 4.5 μg | 83.5 |
| K.35 | 1.5 μg | 83.3 |
| Lipoplex GP | 0.5 μg | 94.9 |

It was observed that use of controlled-release nanocapsules reduced the fraction of apoptotic cells in fibroblast cultures 3 to 100 fold. Conventional reagents without DNA showed a 4-fold increase in FI (Fragmentation Index) over empty nanocapsules, but increased another 50–100% in the presence of additional DNA without additional reagents. Decreasing the coating weight from 1:40 to 1:400 resulted in an increase in average nanocapsule diameter from 20 to 57 nm and the appearance of regions of apoptotic induction in cultures (Table 3: Formula omicron vs. Formula upsilon 35). Decreasing the coating weight from 1:40 to an intermediate 1:100 reduced transduction efficiency without increasing particle size and the appearance of cytotoxicity. These findings indicate that nanocapsule design plays a role in maintaining nanocapsule integrity and that size effects and dissolution profiles can contribute to observed cytotoxicity and functionality. We concluded that application of nanocapsule formulations increased dosing to useful efficiency levels without induction of an apoptotic program.

Table 3B exemplifies this improvement with a dose response of Formula K.35 measured in fibroblast lysates. GFP production was measured in fibroblast lysates after 4 days of treatment with increasing doses of nanocapsules. A 9.5 μg dose of nanocapsules equaled the production of a liposomal formulation without any evidence of cytotoxicity.

Example 4

Nanocapsule Delivery of Macromolecules to Porcine Tissue Across Keratinized Barrier Epithelia by Transdermal and Subcutaneous Means The utility of nanocapsules for nonviral nucleic acid delivery to tissue in a pig biopsy organ culture system was investigated. 6 and 8 mm circular biopsies were collected under sterile conditions from sedated research animals and cultured on meshes in partial contact with media containing 20% Fetal Calf Serum. Biopsies were either injected with 90 μl (6.3 μg) or treated topically with 3×30 μl aliquots. Biopsies were snapfrozen 7 days later and sectioned/homogenized for β-galactosidase production measurement. Formulation information and results from this experiment are summarized in Table 4:

TABLE 4

Functionality of dispersed atomized nanocapsules for macromolecule delivery across keratinized barrier membranes.

| Formula | N | O |
|---|---|---|
| Exp. Modification (from Formula Q) | coating wt. is 2.5x Polymer MW is 1x | coating wt. is 2.5x Polymer MW is 4x |
| Formula Characteristics: | | |
| Nucleic Acid Incorporation (%) | 70.00 | 70.50 |
| Cumulative Release (%, 169 hr 2.5 μg sample | 83 | 83.5 ± 1.5 |
| Low MW DNA in postdigested Electrophoresis Samples | 0 | 0 |
| Supercoil retention (sc) (237 hr release, initial = 69.7% sc/relaxed) | 100% | 100% |
| Particle Size (mean ± SE, major species) | 18.2 ± 0.2 nm | ND |
| Particle Description | spherical | |
| Agglomerates | 20% 100 yeast-like clusters | 20% 100 yeast-like clusters |
| Performance: | | |
| Transduced Protein Production (Shown in FIG. 3B) (pixel units, % of negative control, 100 μg total protein, normalized by protein) | 312 ± 74 (topical) 142 (s.c.) | 191 (topical) |
| Reporter Gene Product Distribution (6.3 μg dose, 6 mm (N), 8 mm (O) porcine biopsy, 1 wk) keratinocytes (% cells), n = 2 fields/200 cells, negative control: 6% | 100% | 100% |

TABLE 4-continued

| Functionality of dispersed atomized nanocapsules for macromolecule delivery across keratinized barrier membranes. | | |
|---|---|---|
| Formula | N | O |
| endothelial cells, (% vwf −+ area) papillary and/or reticular, n = 2–4 fields, negative control: 1.07 ± 0.72 | 73 ± 20 (papillary)*<br>32 ± 15 (reticular)* | 13.8 ± 0.5 (papillary)*<br>8 ± 2 (reticular)* |
| dermis (% area); negative control: 0.24 ± 0.03, n = 4/20x fields | 2.74 ± 0.96* | 1.77 ± 0.49* |

*= $p < 0.05$

Western blotting of radiated tissue lysates showed a 3-fold increase in beta-galactosidase in duplicate biopsies treated topically with Formula N over an identically cultured 6 mm biopsy treated with saline. Only a 2-fold increase was measured in a 8 mm biopsy treated topically with formula O nanocapsules (see FIG. 5A). Formula O was produced with a higher molecular weight analog of the Formula N polymer suggesting a difference in particle morphology, a dose effect or differing in situ release profiles between the two formulations related to this difference. To identify initial cell type-specific differences in nanocapsule delivery effectiveness, tissue sections were analyzed for beta-galactosidase expression in double-label experiments using antibodies to cell-specific epitopes (see FIG. 5B). Digital image analysis of these sections indicated that radiated keratinocytes and endothelial cells are readily transduced in organ culture 7 days after treatment with a 10 day releasing formula. Specific quantitation of fibroblastic cells was not possible without inclusion of a cell-specific marker, however, an 11-fold increase in area of expression was measured in Formula N biopsy dermis (see FIG. 5B). Interestingly, for both the formulae N and O topically-treated biopsies examined, the area percentage of blood vessels transduced decreased about 50% in nearby fields between 100 μm and 300 μm of depth (Table 4: papillary (pap) vs. reticular endothelial (ret) cells). These data suggest that nanocapsules are penetrating the epidermis to enter the dermis.

Example 5

Incorporation of Inventive Nanocapsules into a Solid Dosage Form for Additional Utility in Physical Targeting Nanocapsules containing a nuclear GFP transgene or empty vector were incorporated into a suture coating by vortexing the following components: i) 50 μg of nanocapsules containing plasmid DNA, ii) 200 μg of bovine mucin, and iii) 75 μg of sucrose (60% w/w) in a 1000 μl volume. Sutures were aseptically coated by drawing sutures 5× through punctured microcentrifuge tubes containing the coating. Coating functionality for gene transfer was tested by applying sutures in cultured porcine skin biopsies. Biopsies were cultured on a mesh such that the biopsy bottom was in contact with cell culture media. Biopsies were treated for 7 days, then snap-frozen and sectioned for immunofluorescence microscopy to assess nanocapsule penetration and transgene delivery.

Nanocapsule penetration was detected by streptavidin biotin immunocomplexes directed at sheep IgG. Nanocapsule coatings are spiked with ovine IgG to enable this detection strategy. FIG. 6A shows distribution of sheep IgG signal throughout porcine dermal tissue with accumulation on capillaries. In FIG. 6A', primary antibody is omitted during slide processing to determine level of background fluorescence. A suture is visible in this view. Sutures were identifiable as smooth objects without positive nuclear counterstain. GFP expression was confirmed using a polyclonal GFP antibody to obviate the effect of nonspecific tissue green fluorescence. FIG. 6B shows nuclear-localized GFP expression throughout the suture-treated dermis using a GFP polyclonal antibody. A suture was visible 750 microns away. FIG. 6C shows the lack of GFP expression in a biopsy treated with empty vector coating. This example demonstrates the usefulness of nanocapsules for use in physically targeted macromolecule delivery.

Example 6

Utility of Nanocapsules for Local Targeting by Design of Nanocapsule Coating Fibroblast Targeting GFP nanocapsules were prepared by dispersion atomization as described in Example 1. Polyvinylpyrrolidone (PVP, MW 10,000) was used as the coating basis. A coating weight ratio of 1:40 was used and rod-shaped nanocapsules of 23±2 nm were produced. 1 μg of PVP nanocapsules were applied to both human dermal fibroblasts (HDF) and HacaT keratinocyte cultures for 4 hours then fixed for detection for nanocapsule uptake by streptavidin-biotin immunocomplexes to sheep IgG. Nanocapsule coatings were spiked with ovine IgG to enable this detection strategy. FIG. 7A illustrates positive nuclear localization of PVP nanocapsules in HDF's and negative colocalization of PVP nanocapsules in keratinocytes (FIG. 7A: 7Aa vs. 7Ab). Views of untreated cultures are included for comparison (7A'a, 7A' b). Cultures were also treated with 5 μg of PVP nanocapsules for 5 days then tested for GFP transgene production. Consistent with uptake studies results, only the fibroblast cultures showed production of GFP transgene (7A: 7Aa' vs. 7Ab').

Tumor-targeting

GFP nanocapsules were prepared by dispersion atomization as described in example 1. Tenascin (TN, MW 200,000) was used as the coating basis. A coating weight ratio of 1:20 was used and spherical nanocapsules of 19±0.9 nm were produced. 500 ng of TN nanocapsules were applied topically in successive small aliquots to pig biopsies maintained in organ culture. Biopsies were rinsed in media after 3 minutes of topical application in culture media was changed to preclude any delivery followed by exchange for new media in the organ culture to preclude any delivery other than topical.

To simulate tumor nests of epithelial-derived origin, biopsies had been seeded 12 hours previously with 50,000 human squamous carcinoma cells. 7 days later biopsies were snapfrozen and sectioned for immunological detection of GFP production. In FIG. 7B, view "a" shows intense GFP fluorescence in the tumor center, view "b" confirms this GFP expression with polyclonal antibodies to GFP, view "c" shows cell positioning in the section using a counterstain for cell nuclei and view "d" shows the level of background fluorescence by omission of GFP antibodies. Tumor origin was confirmed by positive detection with antibody to keratin 10/1, an epithelial marker. Comparison of view "b" and view "c" indicates that GFP expression is limited to cells within the tumor. As already demonstrated in example 5, expression throughout a tissue is also feasible and can modulated by coating design. This example demonstrates that nanocapsule delivery can be productively targeted.

Cell-specific Delivery for Enhanced Drug Therapeutic Window

Nanocapsules were prepared as described in Example 1 to encapsulate cisplatin, a hydrophobic molecule and a common cancer chemotherapeutic with serious side effects. A coating weight ratio of 1:100 was used and irregular nanocapsules of 29±3 nm were produced. Targeting efficacy was demonstrated by changes in the dose response for cell growth inhibition in fibroblast vs. squamous cell carcinoma cultures. Cells were seeded overnight into 96 well plates, treated for 18 hours with increasing amounts of encapsulated or naked drug. Drug was then removed and cultures were assessed for cell growth inhibition using an MTT assay 48 hours later for a total growth time of 72 hours. Results are illustrated in FIG. 7C. The data shows that tenascin nanocapsules protected non-target cells from cell death (zero death) at drug levels that killed non-target cells using naked drug (FIG. 7Ca: open vs. closed circles). In carcinoma cultures, TN nanocapsules productively decreased the inhibition concentration (IC50) for cell survival an estimated 200% from 350 to 165 µg/ml. Example 6 demonstrates the usefulness of nanocapsules for use in coating-targeted macromolecule delivery.

Example 7

Utility of Nanoencapsulation for Improved Cellular Uptake of Other Species used as Pharmaceutical, Nutraceutical, Research or Cosmetic Agents Nanocapsules containing either 500 kD Fitc-labeled dextran, 20 mer Fitc-labeled mer O-methylated RNA oligonucleotide and 16 mer phosphodiester DNA oligonucleotide were prepared as described in Example 1. A 1:40 coating weight ratio was used and 1 MM kD recombinant hyaluronan was used a coating basis. PEI was used to condense the phosphodiester DNA oligonucleotide, but no PEI was included in the dextran or RNA oligonucleotide nanocapsule formulas. Nanocapsule functionality for drug delivery was tested by evaluating changes in cellular uptake and lysosomal activity in 35 mm cultures of human dermal fibroblast. Nanocapsule formulas were compared to naked species or species formulated as complexes. Quantitative results are summarized in Table 7.

TABLE 6

| Bioactive Component | Formulation | Particle size (mean, SE, nm, morphology) | 4.5 hours post-addition | | | 18 hours post-addition | |
|---|---|---|---|---|---|---|---|
| | | | Increase in cellular uptake activity, (% cells above baseline, caveolin-1/clathrin) | dose | Nuclear Uptake Efficiency (% cells, fibroblast) | Bioactive component Colocalization with lysosomes, (% cells, human fibroblasts) | Detection persistence, (% cells, human fibroblast) |
| 500 kd fitc-dextran | nanocapsule | 22 ± 2, s/r | 89/20 | 25 µg* | 95 ± 2 | 2 ± 2    5 µg | 88 ± 11 |
| | naked, Fitc-labelled | — | 75/18 | 100 µg | 10 | 100 ± 10   100 µg | 61 ± 20 |
| 20 mer o-methylated RNA oligo | nanocapsule | 13 ± 0.7, r | 78/90 | 2 µg | 74 ± 5 | 0 ± 0   5 µg | 80 ± 6 |
| | naked, Fitc-labelled | — | —/73 | 5 µg | 14 ± 7 | — | — |
| | PEI/Fitc-labelled | 236 ± 26, r | —/— | — | — | 100 ± 0   5 µg | 94 ± 10 |
| 16 mer PO DNA oligo | nanocapsule | 17 ± 1, r | 70/94 | 1 µg | 34 ± 25 | 0 ± 0   5 µg | 91 ± 8 |
| | PEI/Fitc-labelled | 67 ± 4, s/r | 72% lysosomes | 2 µg | 95 ± 2 | 80 ± 7   5 µg | 66 |
| Nominal n | | 20 particles | 70 cells | | 140 cells | 50 cells | 50 cells |

Nanoencapsulation improves cellular uptake of other species used as pharmaceutical, nutraceutical, research or cosmetic agents.
At 18 hours post-addition, lysosomes are only evident in conventionally formulated species.
*Dose was estimated for encapsulation dextran assuming 100% encapsulation.
s = sphere
r = rod Table 7 shows that average diameters for all nanocapsules were below 50 nm by AFM. PEI complexes of DNA oligonucleotides were measured at 67 nm and PEI complexes of uncharged RNA O-methyl oligonucleotides were measured at 236 nm. As discussed in Example 2 using keratinocyte cultures and plasmid DNA, nanocapsules stimulate uptake activity as indicated by increased signal levels of clathrin and caveolin-1. In the 500 kD dextran case, uptake activity shifts productively towards caveolae and potocytosis with nanoencapsulation (Table 7, 500 kD Dextran). At 4.5 hours post-addition, nuclear uptake is enhanced for encapsulated dextran and RNA relative to naked species.

For the case of DNA oligonucleotides, cellular uptake of the nanoencapsulated oligonucleotides is decreased relative to complexed oligonucelotides. However, by 4.5 hours post-addition, a majority of the simply complexed DNA oligonucleotide is already nonproductively sequestered in lysosomes (Table 7). At 18 hours post-addition, nanocapsule species show continued exclusion from lysosomes, while the DNA oligonucleotide polyplexes show high levels of sequestration.

This pattern of nanocapsule exclusion from lysosomes and polyplex sequestration in lysosomes is illustrated in FIGS. 8A and 8B for an O-methyl RNA oligonucleotide species labeled with fluorescein (Fitc). Views 8Aa and 8Ba show fluorescein detection in cultures at 18 hours post-addition indicating that distribution is exclusively nuclear for the nanocapsules of RNA oligonucleotides. Punctate inclusions are visible that co-localize with an immunological marker for lysosomes in the cultures treated with RNA oligonucleotide polyplexes (FIG. 8A:a vs a'). Particle sizing results from AFM microscopy for polyplexes and nanocapsules are included to the dramatic differences in sizing following nanoencapsulation. (FIGS. 8A, 8B:8Ab vs.8Bb, 8Bb'). Formulas encapsulating lower molecular weight dextrans and unstabilized RNA were also prepared with similar uptake, nanocapsule size and yield to demonstrate that nanoencapsulation can provide not only a targeting function but aid in stabilizing molecules sensitive to chemical or enzymatic degradation. These examples demonstrates the usefulness of nanocapsules 36 for use in delivery of a broad range of macromolecules.

Although the present invention has been described with reference to preferred embodiments, workers skilled in the art will recognize that changes may be made in form and detail without departing from the spirit and scope of the invention.

What is claimed is:

1. A method of forming a dispersion of micelles, the method comprising:
   forming a plurality of surfactant micelles, wherein the plurality of surfactant micelles comprises:
   a surfactant associated with coating a surface of a bioactive component, wherein the surfactant has an HLB value of less than about 6.0 units; and
   dispersing the surfactant micelles into an aqueous composition, wherein the aqueous composition comprises a hydrophilic polymer, wherein the hydrophilic polymer associates with the surfactant micelles to form stabilized surfactant micelles having an average diameter of less than about 50 nanometers.

2. The method of claim 1 wherein the surfactant molecule is a non-ionic surfactant.

3. The method of claim 1 wherein the bioactive component is a hydrophilic component.

4. The method of claim 1 wherein the bioactive component is a polynucleotide or a polypeptide.

5. The method of claim 1 wherein the bioactive component is a carbohydrate or a hydrophobic bioactive molecule.

6. The method of claim 1 wherein the bioactive component consists essentially of a fluorescent molecule.

7. The method of claim 1 and further including precipitating the stabilized surfactant micelles to form particles having an average diameter of less than about 50 nanometers as measured by atomic force microscopy of the particles following drying of the particles.

8. The method of claim 7 wherein the bioactive component is partitioned from the hydrophilic polymer in the particles.

9. The method of claim 7 and further including incubating the particles in the presence of at least one cation.

10. The method of claim 9 wherein the at least one cation comprises lithium.

11. A method of forming a dispersion of surfactant micelles, the method comprising:
dispersing surfactant molecules into a first hydrophilic composition, the first hydrophilic composition comprising a hydrophilic bioactive component, wherein the surfactant molecules have an HLB value of less than about 6.0 units, and wherein the surfactant molecules form a shell around the hydrophilic bioactive component to form a dispersion of surfactant micelles;
adding a biocompatible hydrophilic polymer to the dispersion of surfactant micelles; and
wherein the biocompatible hydrophilic polymer stabilizes the dispersion.

12. The method of claim 11 wherein the biocompatible hydrophilic polymer forms a shell around the surfactant micelle.

13. A method of forming a particle, the method comprising:
dispersing a surfactant molecule into an aqueous composition comprising a hydrophilic bioactive component, wherein the surfactant molecule has an HLB value of less than about 6.0 units, and wherein the surfactant molecule is associated with the hydrophilic bioactive component to form a plurality of surfactant micelles;
exposing the surfactant micelles to a biocompatible polymer to form a plurality of stabilized surfactant micelles; and
solidifying the stabilized surfactant micelles to form particles by exposing the stabilized surfactant micelles to at least one cation, wherein the particles have an average diameter of less than about 50 nanometers as measured using atomic force microscopy of the particles following drying of the particles.

14. The method of claim 13 wherein the surfactant molecule has a critical micelle concentration of less than about 200 micromolar.

15. The method of claim 13 wherein the biocompatible polymer forms a shell around the surfactant micelle.

16. The method of claim 13 further comprising dispersing droplets comprising stabilized surfactant micelles into a second aqueous composition.

17. The method of claim 13 wherein the hydrophilic bioactive component is condensed.

18. The method of claim 13 wherein the biocompatible polymer is associated with or comprises a cell recognition component.

19. The method of claim 13 wherein the bioactive component is a carbohydrate or a hydrophobic bioactive molecule.

20. The method of claim 13 wherein the bioactive component consists essentially of a fluorescent molecule.

21. The method of claim 13 and further including dispersing the surfactant molecule into a biocompatible oil prior to dispersing the surfactant molecule into the aqueous composition.

22. The method of claim 13 further comprising:
combining a plurality of the particles, with a binder and an excipient to form a matrix capable of releasing the particles.

23. The method of claim 13 wherein the surfactant molecule is at a concentration of less than about 500 parts per million.

24. The method of claim 22 and further including applying, pellitizing, tableting, or granulating the matrix.

25. A particle prepared by the method of claim 13.

26. A method of making a particle, the method comprising:
condensing a bioactive component to form a condensed bioactive component;
dispersing a surfactant into an aqueous composition comprising the condensed bioactive component, wherein the surfactant has an HLB value of less than about 6.0 units, and wherein the surfactant associates with the condensed bioactive component to form a plurality of surfactant micelles;
exposing the surfactant micelles to a biocompatible polymer to form a plurality of stabilized surfactant micelles; and
precipitating the stabilized surfactant micelles to form particles having an average diameter of less than about 50 nanometers as measured by atomic force microscopy of the particles following drying of the particles;
wherein the bioactive component comprises DNA or a polypeptide.

27. The method of claim 26 wherein the biocompatible polymer is an iontophoretic polymer.

28. The method of claim 26 and further including decreasing the average size of the particles by incubating the particles in the presence of a cation.

29. A method of preparing particles, the method comprising:
forming a plurality of hydrophobic compositions, wherein the hydrophobic composition comprises a surfactant associated with a bioactive hydrophobic component, and wherein the surfactant has an HLB value of less than about 5.0 units;
adding a biocompatible polymer to the hydrophobic composition to form a stabilized composition; and
precipitating the stabilized composition to form a particle having an average diameter of less than about 50 nanometers as measured using atomic force microscopy of dried particles.

30. The method of claim 29 wherein the biocompatible polymer is capable of iontophoretic exchange.

31. The method of claim 29 wherein the hydrophobic composition further includes a water-miscible solvent.

32. The method of claim 29 further comprising mechanically forming a plurality of droplets of the stabilized composition; and
dispersing the plurality of droplets into an aqueous composition.

33. The method of claim 29 wherein the surfactant is 2,4,7,9-tetramethyl-5-decyn-4,7-diol, molecules containing an acetylenic diol portion, or blends of 2,4,7,9-tetramethyl-5-decyn-4,7-diol.

34. The method of claim 29 wherein the hydrophobic component is entangled or embedded in the biocompatible polymer.

35. The method of claim 29 and further including filtering the particles.

36. The method of claim 29 wherein the biocompatible polymer is a hydrophilic polymer.

37. The method of claim 29 and wherein precipitating the particles in the presence of at least one cation.

38. The method of claim 29 and further including adding the particles into a solid dosage form.

39. The method of claim 36 and further including centrifuging the particles.

40. The method of claim 37 wherein incubating the particles reduces the average diameter of the particles.

41. The method of claim 38 wherein the solid dosage form is selected from the group consisting of granules, tablets, pellets, films and coatings.

42. A particle prepared by the method of claim 29.

43. A method of forming a particle, the method comprising:
- dispersing a surfactant molecule into an aqueous composition comprising a hydrophilic bioactive component, wherein the surfactant molecule has an HLB value of less than about 5.0 units, and exposing the surfactant molecule to the hydrophilic component to form a plurality of surfactant micelles;
- adding a biocompatible polymer to the plurality of surfactant micelles to form a plurality of stabilized surfactant micelles;
- solidifying the stabilized surfactant micelles to form a plurality of particles by exposing the stabilized surfactant micelles to at least one cation, wherein the particles have an average diameter of less than about 50 nanometers as measured by atomic force microscopy of the particles following drying of the particles; and
- applying a cell recognition component to the particles.

44. A method of forming a targeted particle, the method comprising:
- dispersing a surfactant molecule into an aqueous composition comprising a bioactive molecule, wherein the surfactant molecule has an HLB value of less than about 6.0 units, and wherein the surfactant molecule associates with the bioactive molecule to form a surfactant micelle;
- adding a biocompatible polymer and a cell recognition component to the surfactant micelle to form a stabilized aqueous composition comprising a plurality of stabilized surfactant micelles; and
- exposing the stabilized surfactant micelles to at least one cation to precipitate the stabilized surfactant micelles to form particles having an average diameter of less than about 50 nanometers as measured by atomic force microscopy of the particles following drying of the particles.

45. A method of forming a particle, the method comprising:
- dispersing a surfactant molecule into an aqueous composition comprising a hydrophilic biocompatible component, wherein the surfactant molecule has an HLB value of less than about 6.0 units, and wherein the surfactant molecule is associated with the hydrophilic biocompatible component to form a plurality of surfactant micelles;
- exposing the surfactant micelles to a biocompatible polymer to form a plurality of stabilized surfactant micelles; and
- solidifying the stabilized surfactant micelles to form particles by exposing the stabilized surfactant micelles to at least one cation, wherein the particles have an average diameter of less than about 50 nanometers as measured using atomic force microscopy of the particles following drying of the particles.

46. The method of claim 45 further including adding the particles into a solid dosage form.

47. The method of claim 45 wherein the biocompatible polymer is associated with or comprises a cell recognition component.

* * * * *